(12) United States Patent
Sato et al.

(10) Patent No.: US 11,345,556 B2
(45) Date of Patent: May 31, 2022

(54) SHEET CONVEYING DEVICE AND SHEET PROCESSING DEVICE PROVIDED WITH SAME, AND METHOD FOR CONVEYING SHEET AND METHOD FOR PROCESSING SHEET USING SHEET CONVEYING DEVICE

(71) Applicant: ZUIKO CORPORATION, Osaka (JP)

(72) Inventors: Hitoshi Sato, Osaka (JP); Takashi Arima, Osaka (JP); Kouji Utani, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 323 days.

(21) Appl. No.: 16/613,228

(22) PCT Filed: May 11, 2018

(86) PCT No.: PCT/JP2018/018336
§ 371 (c)(1),
(2) Date: Nov. 13, 2019

(87) PCT Pub. No.: WO2018/212092
PCT Pub. Date: Nov. 22, 2018

(65) Prior Publication Data
US 2020/0172361 A1    Jun. 4, 2020

(30) Foreign Application Priority Data

May 16, 2017    (JP) .............................. JP2017-097344

(51) Int. Cl.
*B65H 5/22*    (2006.01)
*A61F 13/15*    (2006.01)
(Continued)

(52) U.S. Cl.
CPC ....... *B65H 5/226* (2013.01); *A61F 13/15601* (2013.01); *A61F 13/15723* (2013.01);
(Continued)

(58) Field of Classification Search
CPC .... B65H 5/226; B65H 27/00; B65H 35/0086; A61F 13/15723; A61F 13/15764;
(Continued)

(56) References Cited

U.S. PATENT DOCUMENTS 4,726,876 A * 2/1988 Tomsovic, Jr. ... A61F 13/15601
198/459.8
5,091,039 A * 2/1992 Ujimoto ............... B65G 47/848
156/519

(Continued)

FOREIGN PATENT DOCUMENTS

CN         1356097      7/2002
CN       104427961      3/2015
(Continued)

OTHER PUBLICATIONS

International Search Report dated Jun. 19, 2018 in International (PCT) Application No. PCT/JP2018/018336.

*Primary Examiner* — Michael A Tolin
*Assistant Examiner* — Christopher C Caillouet
(74) *Attorney, Agent, or Firm* — Wenderoth, Lind & Ponack, L.L.P.

(57) ABSTRACT

A sheet conveying device includes: a holding mechanism configured to hold suction members; and a driving device including a rotary shaft which is rotatable about a second axis parallel to the first axis and a connecting mechanism configured to connect the rotary shaft and suction members to each other; and a support mechanism configured to support the holding mechanism and the drive device. The connecting mechanism is connected to the suction members in a state where the suction members are movable in a radial direction of the circle about the first axis. The support mechanism supports the holding mechanism and the drive device such that the holding mechanism and the drive device (Continued)

are relatively movable from each other in a direction orthogonal to the first axis.

20 Claims, 17 Drawing Sheets

(51) Int. Cl.
    *B65H 27/00*     (2006.01)
    *B65H 35/00*     (2006.01)

(52) U.S. Cl.
    CPC .. *A61F 13/15756* (2013.01); *A61F 13/15764* (2013.01); *A61F 13/15772* (2013.01); *B65H 27/00* (2013.01); *B65H 35/0086* (2013.01); *A61F 2013/15788* (2013.01); *A61F 2013/15926* (2013.01)

(58) Field of Classification Search
    CPC ............... A61F 13/15; A61F 13/15601; A61F 13/15772; A61F 2013/15788; A61F 2013/15926
    See application file for complete search history.

(56) References Cited

U.S. PATENT DOCUMENTS

| | | |
|---|---|---|
| 5,716,478 A | 2/1998 | Boothe et al. |
| 5,759,340 A | 6/1998 | Boothe et al. |
| 6,620,276 B1 | 9/2003 | Kuntze et al. |
| 9,511,951 B1* | 12/2016 | Schneider .............. B65G 29/02 |
| 2002/0103468 A1 | 8/2002 | Nakakado et al. |
| 2008/0196564 A1* | 8/2008 | McCabe ........... A61F 13/15764 83/152 |
| 2011/0319243 A1 | 12/2011 | Fujita |
| 2015/0223992 A1 | 8/2015 | Maehara et al. |

FOREIGN PATENT DOCUMENTS

| | | |
|---|---|---|
| JP | 64-8184 | 1/1989 |
| JP | 11-513647 | 11/1999 |
| JP | 2002-521091 | 7/2002 |
| JP | 5604743 | 10/2014 |

\* cited by examiner

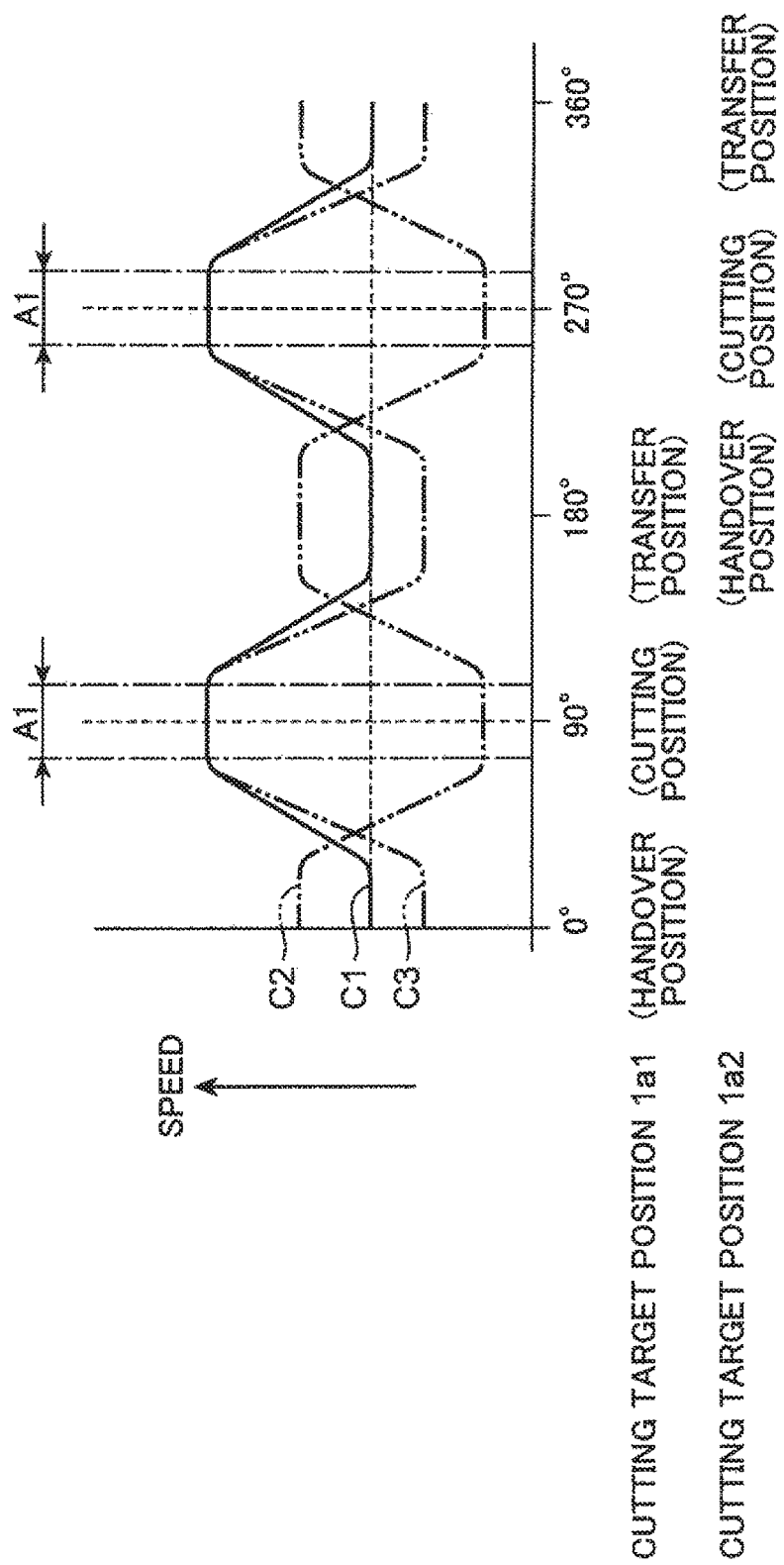

SHEET CONVEYING DEVICE AND SHEET PROCESSING DEVICE PROVIDED WITH SAME, AND METHOD FOR CONVEYING SHEET AND METHOD FOR PROCESSING SHEET USING SHEET CONVEYING DEVICE

TECHNICAL FIELD

The present invention relates to a sheet conveying device for continuously conveying a sheet in a longitudinal direction of the sheet.

BACKGROUND ART

Conventionally, there has been known a cutting device which cuts a sheet continuously conveyed in a longitudinal direction at a predetermined pitch.

For example, a system described in Patent Literature 1 includes: a drum which receives a continuously conveyed sheet at a predetermined receiving position and holds the sheet by suction, and a cutting device which is disposed on a peripheral surface of the drum in an oppositely facing manner and cuts the sheet held on the drum by suction.

The drum includes: a plurality of holding surface arranged along a peripheral surface of the drum; and a plurality of anvils respectively disposed between the holding surfaces, and is configured to rotate the holding surfaces and the anvils.

The cutting device includes a cutter roller for cutting the sheet between the cutting device and the anvils.

In the system described in Patent Literature 1, the sheet is cut at a cutting pitch at which the respective anvils sequentially oppositely face the cutter roller in response to the rotation of the drum. Accordingly, a product length of the sheet cut by the cutter roller (a length of the sheet released from a tension) is defined by a length of the sheet positioned within the cutting pitch at a point of time when the sheet is held by suction at a position where the drum is received.

In such a system, in the case where it is necessary to increase the product length of the sheet, for example, considered is the case where the cutting pitch at which the anvils and the cutter roller sequentially oppositely face each other is increased.

However, to increase such a cutting pitch, it is necessary to increase a radius of the drum. That is, it is necessary to change the arrangement of the cutter roller together with an exchange of the drum. Accordingly, an operation for changing the cutting pitch becomes extremely cumbersome.

In view of the above, there has been a demand for a conveying device which conveys a sheet to a device such as the drum described in Patent Literature 1, in which a length of the sheet handed over to the device on a downstream side can be easily changed at the time of handing over the sheet to the drum.

CITATION LIST

Patent Literature

Patent literature 1: Japanese Patent No. 5604743

SUMMARY OF INVENTION

It is an object of the present invention to provide a sheet conveying device capable of easily changing a length of a sheet which is handed over to a device disposed on a downstream side at the time of handing over the sheet to the device on the downstream side, a sheet processing device provided with the sheet conveying device, and a method for conveying a sheet and a method for processing a sheet using the sheet conveying device.

To overcome the above-mentioned problems, the present invention provides a sheet conveying device for continuously conveying a sheet so as to hand over the sheet to a device disposed on a downstream side, the sheet conveying device including: a plurality of suction members each having a suction surface capable of sucking the sheet; a holding mechanism configured to hold the plurality of suction members in a state where the suction surfaces are arranged in a spaced-apart manner from each other along a circumference of a circle about a first axis and the plurality of suction members is rotatable about the first axis; a drive device having: a rotary shaft being rotatable about a second axis which is parallel to the first axis; and a connecting mechanism configured to connect the rotary shaft and the plurality of suction members to each other such that power from the rotary shaft is transmittable to the plurality of suction members; and a support mechanism configured to support the holding mechanism and the drive device, wherein the connecting mechanism is connected to the plurality of suction members in a state where the plurality of the suction members is movable in a radial direction of the circle about the first axis, and the support mechanism supports the holding mechanism and the drive device such that the holding mechanism and the drive device are relatively movable from each other in a direction orthogonal to the first axis.

The present invention further provides a sheet processing device for cutting a sheet at a predetermined length, the sheet processing device including: the sheet conveying device; and a cutting device configured to receive the sheet from the sheet conveying device and cut the sheet at a predetermined pitch.

The present invention provides a method for conveying a sheet using the sheet conveying device, the method including: a first conveying step of conveying the sheet while making the sheet sucked to the suction surfaces of the plurality of suction members by rotatably driving the rotary shaft about the second axis and thus rotating the plurality of suction members about the first axis; a stopping step of stopping rotary driving of the rotary shaft; a moving step of moving connecting positions between the connecting mechanism and the plurality of suction members in a radial direction of a circle about the first axis by moving the holding mechanism and the drive device relative to each other in a direction orthogonal to the first axis by the support mechanism; and a second conveying step of conveying the sheet by rotatably driving the rotary shaft again about the second axis.

The present invention further provides a method for processing a sheet using the sheet conveying device, and a cutting device for receiving the sheet from the sheet conveying device and cutting the sheet at a predetermined pitch, the method including: a first conveying step of conveying the sheet while making the sheet sucked to the suction surfaces of the plurality of suction members by rotatably driving the rotary shaft about the second axis and thus rotating the plurality of suction members about the first axis; a first cutting step of cutting the sheet conveyed in the first conveying step using the cutting device; a stopping step of stopping rotary driving of the rotary shaft; a moving step of moving connecting positions between the connecting mechanism and the plurality of suction members in a radial direction of a circle about the first axis by moving the holding mechanism and the drive device relative to each other in a direction orthogonal to the first axis by the support mechanism; a second conveying step of conveying the sheet by rotatably driving the rotary shaft again about the second axis; and a second cutting step of cutting the sheet conveyed in the second conveying step using the cutting device.

According to the present invention, at the time of handing over a sheet to a device on a downstream side, a length of the sheet handed over to the device on the downstream side can be easily changed.

BRIEF DESCRIPTION OF DRAWINGS

FIG. 16 is a side view showing a cutting state of the sheet in the processing device shown in

FIG. 13.

FIG. 17 is a chart showing a speed control performed by a controller shown in FIG. 13.

DESCRIPTION OF EMBODIMENTS

Hereinafter, an embodiment of the present invention is described with reference to attached drawings. The following embodiment is an example which embodies the present invention, and is not intended to limit the technical scope of the present invention.

Figure 1:
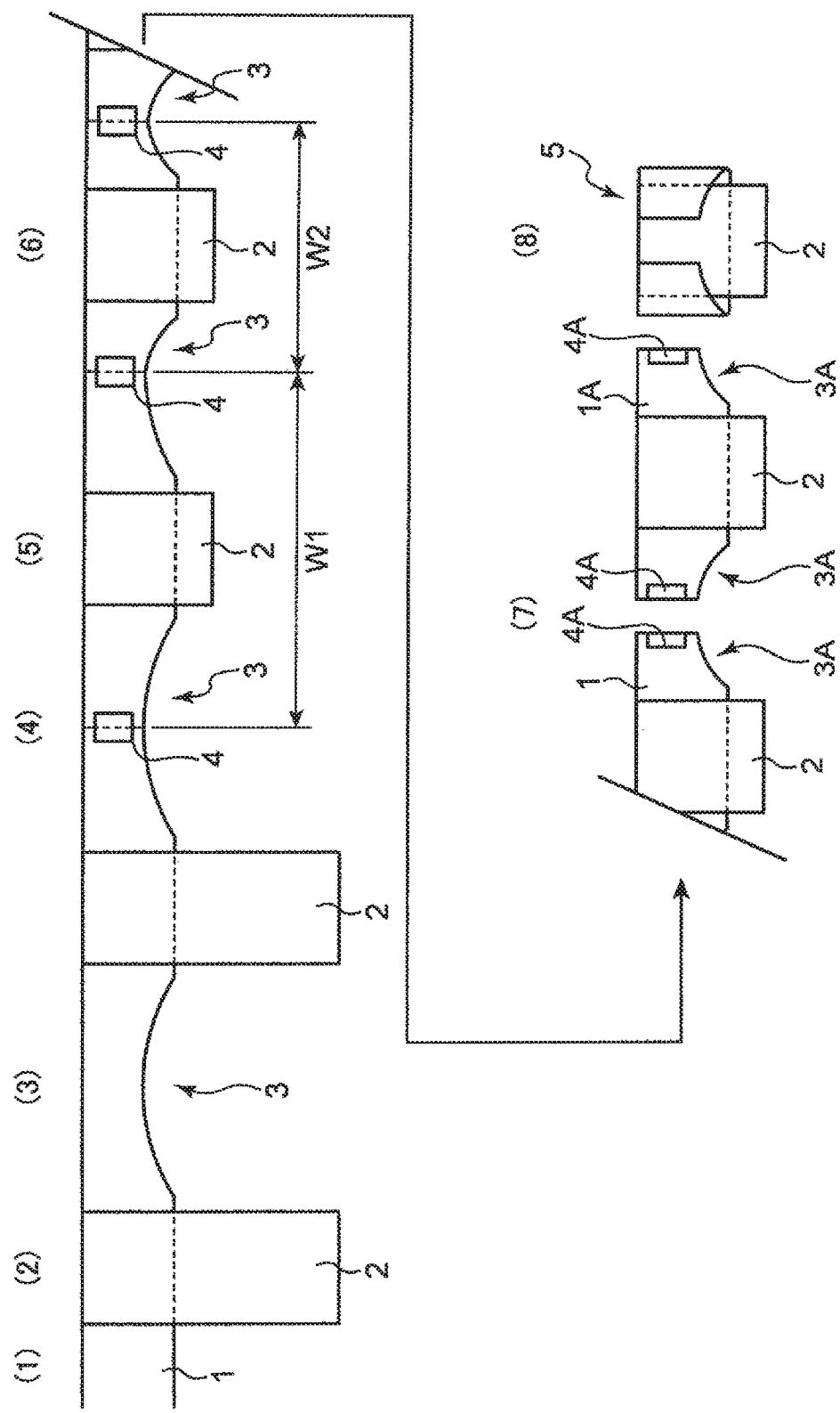
FIG. 1 is a step view showing a method for manufacturing a disposable diaper.

Firstly, with reference to FIG. 1, the description is made with respect to a method for manufacturing disposable diapers 5 manufactured using a sheet 1 conveyed by a conveying device according to an embodiment of the present invention.

The method for manufacturing the disposable diapers 5 includes steps (1) to (8).

In step (1), the sheet 1 formed using an unwoven fabric or the like is conveyed along a longitudinal direction. Step (1) is performed continuously until step (7) described later where the sheet 1 is cut in a state where tension is applied to the sheet 1 in the longitudinal direction of the sheet 1. The sheet 1 may include an elastic member disposed in a stretched state along the longitudinal direction of the sheet 1.

In step (2), a diaper body 2 is adhered to a skin side surface of the conveyed sheet 1 (a surface of the sheet 1 which faces a wearer side when the wearer wears the disposable diaper 5 (a front side surface of the sheet 1 in FIG. 1), the same definition being applicable hereinafter). Specifically, the diaper body 2 is adhered to the skin side surface of the sheet 1 in a state where the diaper body 2 is positioned such that a longitudinal direction of the diaper body 2 is orthogonal to the longitudinal direction of the sheet 1. The diaper body 2 is a portion which extends from a front abdominal portion to a rear dorsal portion by way of a crotch of a wearer in the disposable diaper 5 after completion. The diaper body 2 may include an absorbent core for absorbing an excrement, and an elastic member for improving fitting property for a wearer.

In step (3), notches 3 for a leg use are formed in the sheet 1. The notch 3 for a leg use is provided for forming an edge portion of the sheet 1 extending along a root portion of a thigh of a wearer in the disposable diaper 5 after completion.

In step (4), a hook and loop fastener 4 is adhered to the skin side surface of the sheet 1 at an intermediate position of two diaper bodies 2 disposed adjacently to each other. The hook and loop fastener 4 is formed such that the hook and loop fastener 4 engages with an opposite skin side surface (a surface of the diaper body 2 which faces a side opposite to a wearer when the wearer wears the disposable diaper 5, the same definition being applicable hereinafter) of the diaper body 2. In this embodiment, the opposite skin side surface of the diaper body 2 includes an unwoven fabric and hence, the hook and loop fastener 4 is directly engageable with the opposite skin side surface of the diaper body 2. A hook and loop fastener which is engageable with the hook and loop fastener 4 may be mounted on the opposite skin side surface of the diaper body 2.

In step (5), the diaper body 2 is folded in half in the longitudinal direction of the diaper body 2. Accordingly, the opposite skin side surface of the diaper body 2 faces a front side in FIG. 1.

In step (6), a length of the sheet 1 to be held by suction by two suction surfaces disposed adjacently to each other of a sheet conveying device 10 described later is adjusted corresponding to a size (for example, one of a small size, a middle size and a large size) of the disposable diaper 5 which is an object to be manufactured. In step (7) described later, the sheet 1 is cut at a preset cutting pitch. Accordingly, by increasing a length of the sheet 1 having a natural length (the sheet 1 in a state where a tension is not applied) which is positioned within the cutting pitch in step (6), the disposable diaper 5 having a large size can be manufactured. On the other hand, by decreasing a length of the sheet 1 having a natural length positioned within the cutting pitch in step (6), the disposable diaper 5 having a small size can be manufactured. In the example shown in FIG. 1, a tension applied to the sheet 1 is decreased such that a width size W1 of the sheet 1 held by suction becomes a width size W2 which is smaller than the width size W1. Accordingly, a length of the sheet 1 positioned within the cutting pitch can be decreased and hence, the disposable diaper 5 having a small size can be manufactured.

In step (7), the sheet 1 is cut at a preset cutting pitch. Accordingly, the sheet 1 can be cut at a width corresponding to a size (for example, one of a small size, a middle size and a large size) of the disposable diaper 5 which is determined based on the cutting pitch and the width size W2 adjusted in step (6). In step (7), the hook and loop fastener 4 is also cut such that the hook and loop fastener 4 remains on two disposable diapers 5 disposed adjacently to each other. In the case where the disposable diaper 5 having a size which is determined based on the cutting pitch and the width size W1 is manufactured, the step in the above-mentioned step (6) can be omitted (a first axis J1 and a second axis J2 can be disposed on the same line in the conveying device 10 described later).

In step (8), portions protruding from both sides of the diaper body 2 on the sheet 1 cut in step (7) (hereinafter referred to as flap portions) are respectively folded back such that these portions overlap with the diaper body 2. Accordingly, the hook and loop fasteners 4 engage with the opposite skin side surface of the diaper body 2 so that the disposable diaper 5 is completed.

Figure 2:
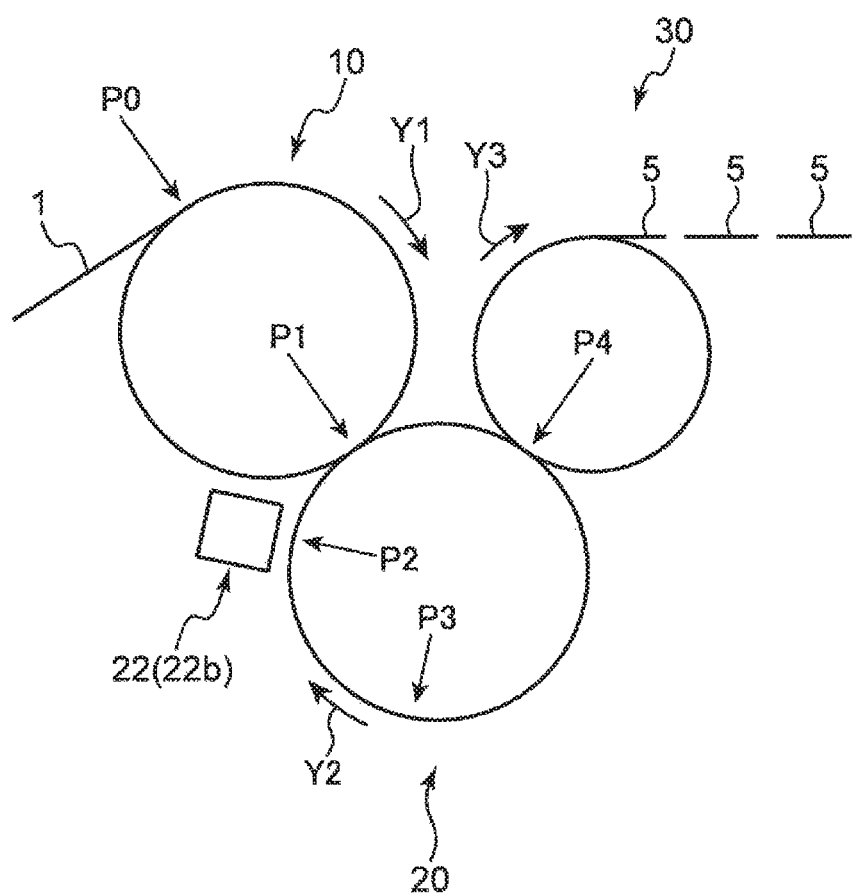
FIG. 2 is a side view showing a portion of a processing device used in the method for manufacturing shown in FIG. 1.

FIG. 2 is a schematic side view showing a processing device which performs the above-mentioned steps (6) to (8).

With reference to FIG. 1 and FIG. 2, the processing device includes: the conveying device 10 which receives the sheet 1, to which step (5) is applied, at a receiving position P0 and performs step (6); a cutting device 20 which receives the sheet 1 from the conveying device 10 at a handover position P1 and performs step (7) and step (8); and a transfer device 30 which receives the disposable diaper 5 from the cutting device 20 at a transfer position P4 and transfers the disposable diaper 5 to a step on a downstream side.

Figure 4:
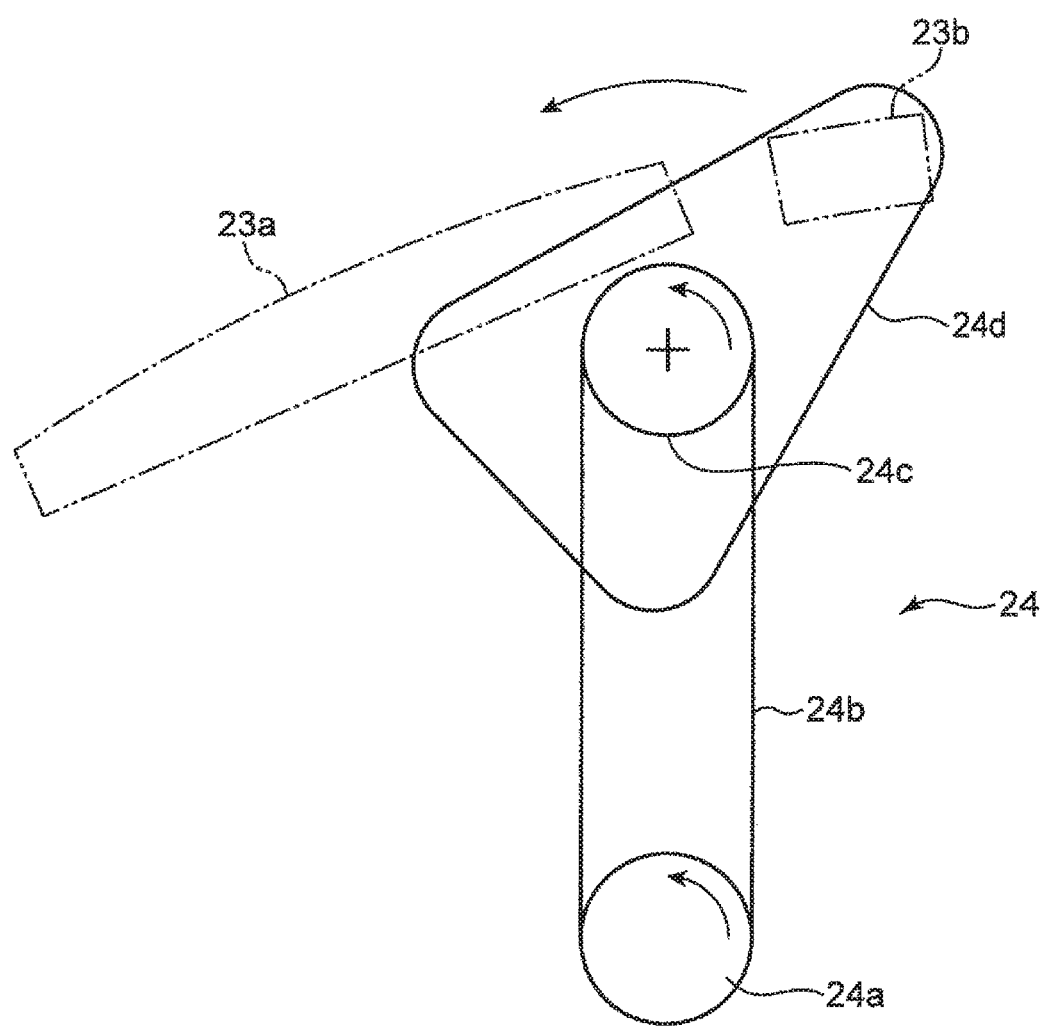
FIG. 4 is a side view showing the configuration for driving the folding pads shown in FIG. 3.
Figure 5:
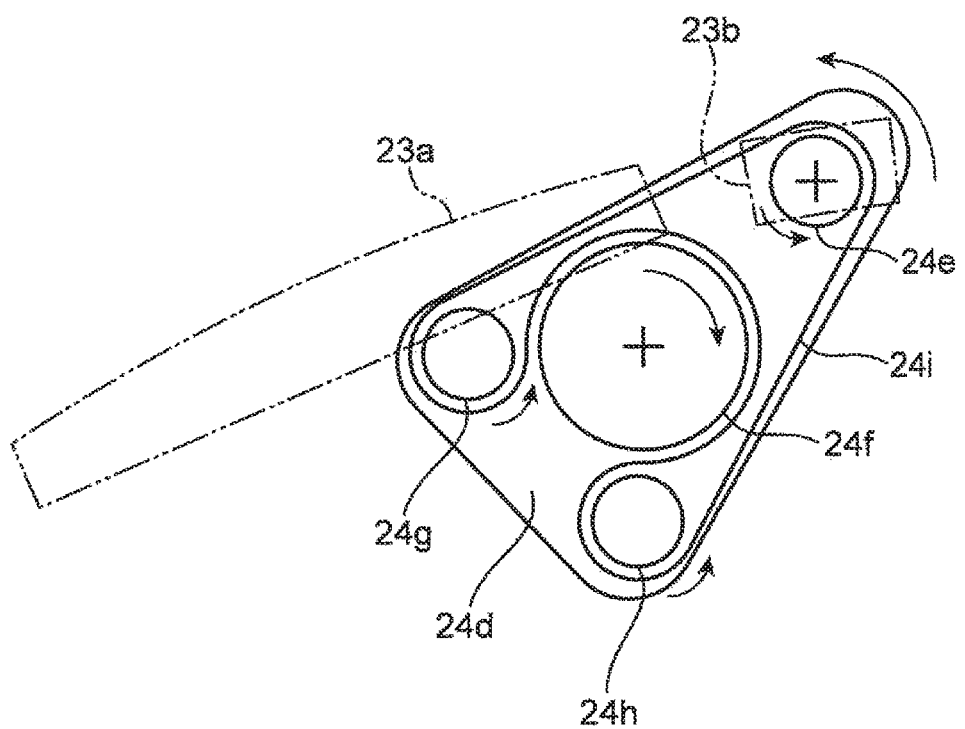
FIG. 5 is a side view showing the configuration for driving the folding pads shown in FIG. 3.

Firstly, the cutting device 20 is described with reference to FIG. 3 to FIG. 5. The cutting device 20 receives (holds by suction) the sheet 1 from the conveying device 10, and cuts the sheet 1 at a predetermined cutting pitch. Specifically, the cutting device 20 includes: a conveying drum 21 for conveying the sheet 1; and a cutting unit 22 for cutting the sheet 1 being conveyed by the conveying drum 21.

The conveying drum 21 includes: a plurality of suction units 23 which hold the sheet 1 by suction; a fold-back drive mechanism 24 which drives the suction units 23 for performing step (8); and a holding mechanism (not shown) which holds the suction units 23 and the fold-back drive mechanism 24 in a rotatable manner in a direction indicated by an arrow Y2 about a preset rotary axis. The holding mechanism holds the plurality of suction units 23 such that suction surfaces of the plurality of suction units 23 are disposed on the same circumference and the plurality of suction units 23 are rotatable, the suction surfaces being for sucking the sheet 1.

The suction unit 23 includes: a body sucking part 23a which sucks a portion of the sheet 1 to which the diaper body 2 is adhered; and a pair of flap sucking parts 23b for sucking portions of the sheet 1 corresponding to the flap portions.

The fold-back drive mechanism 24 drives the flap sucking parts 23b such that the flap sucking parts 23b overlap with the sheet 1 (diaper body 2) sucked by the body sucking part 23a. Specifically, as shown in FIG. 4 and FIG. 5, the fold-back drive mechanism 24 includes; a pair of pulleys 24a, 24c supported by the holding mechanism not shown; an endless belt 24b extended between and wound around the pulleys 24a, 24c; a rotary arm 24d fixed to the pulley 24c; four pulleys 24e to 24h supported on the rotary arm 24d; and an endless belt 24i extended between and wound around the pulleys 24e to 24h. A motor not shown is connected to the pulley 24a. When the pulley 24a is rotated in a direction indicated by an arrow in FIG. 4 due to a driving force of the motor, the pulley 24c is rotated in a direction indicated by an arrow by way of the endless belt 24b. When the pulley 24c is rotated, the rotary arm 24d fixed to the pulley 24c is rotated in a direction indicated by an arrow in FIG. 4. The flap sucking part 23b is fixed to a distal end portion of the rotary arm 24d. Accordingly, in response to the rotation of the pulley 24c, the flap sucking part 23b moves to the outside of the body sucking part 23a (outside in a radial direction of a circle about the rotary axis set in the holding mechanism). Further, as shown in FIG. 5, a motor not shown is also connected to the pulley 24f mounted on the rotary arm 24d. When the pulley 24f is rotated in a direction indicated by an arrow by the motor, the pulley 24e is rotated in a direction indicated by an arrow by way of the endless belt 24i. The flap sucking part 23b is mounted on the pulley 24e in a state where the flap sucking part 23b is rotatable about a rotary axis of the pulley 24e. Accordingly, in response to the rotation of the pulley 24e, a portion of the sheet 1 sucked by the pulley 24e can be folded back on the sheet 1 (diaper body 2) sucked by the body sucking part 23a, the portion corresponding to the flap portion. Due to the above-mentioned operation of the fold-back drive mechanism 24, as shown in FIG. 3, when the conveying drum 21 is rotated to a fold-back position P3, a fold-back operation of the flap portion, that is, step (8) is performed.

Figure 3:
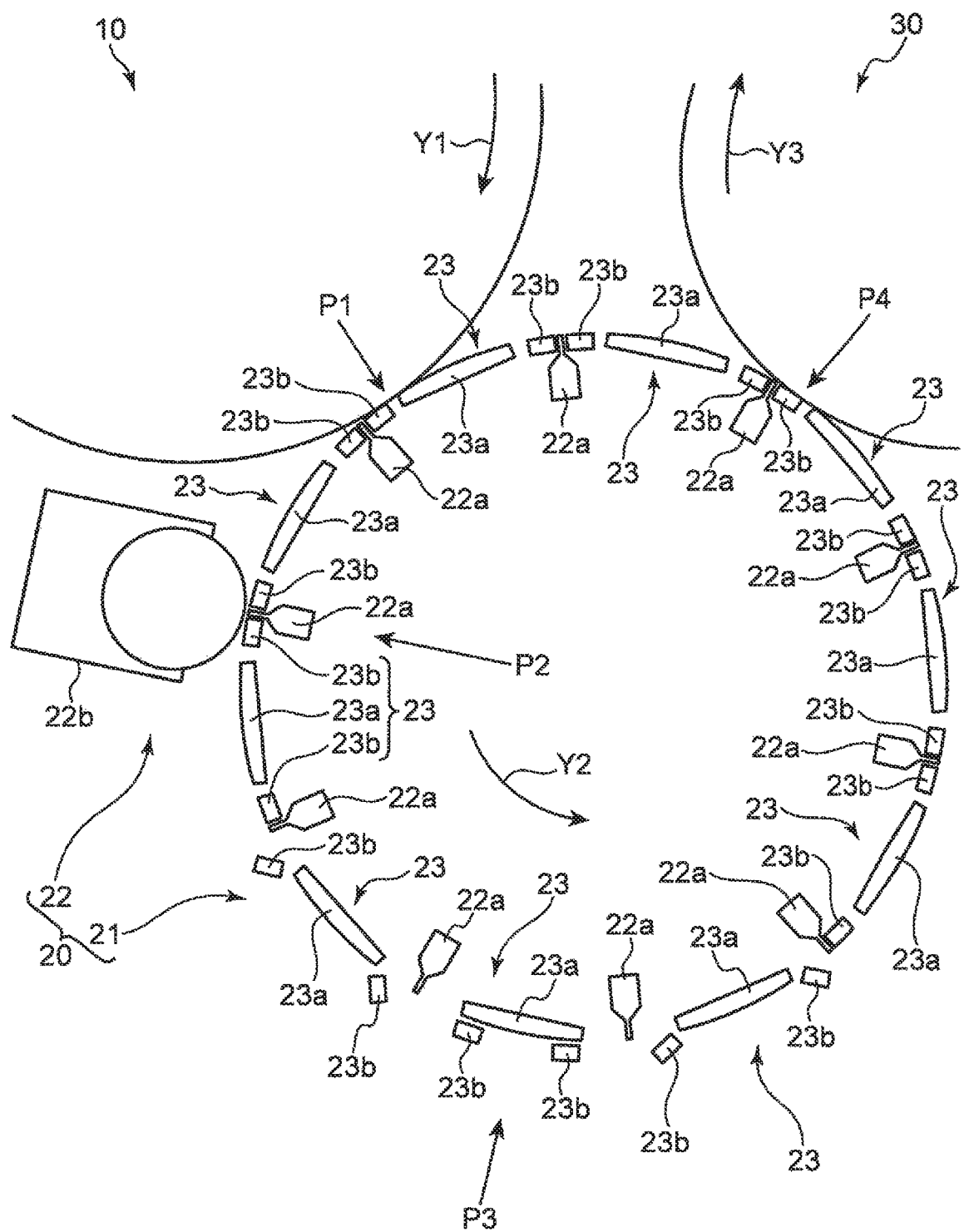
FIG. 3 is a side view showing a cutting device shown in FIG. 2 in an enlarged manner.

With reference to FIG. 3, the cutting unit 22 includes: a plurality of anvils 22a held by the holding mechanism of the conveying drum 21 such that the anvil 22a is positioned between the suction units 23; and a rotary cutter 22b disposed so as to face the anvil 22a at a cutting position P2 preset as the position for cutting the sheet 1.

The plurality of anvils 22a are arranged at an equal interval about the rotary axis of the conveying drum 21, and are rotated about the rotary axis. Accordingly, along with the rotation of the conveying drum 21, the respective anvils 22a sequentially face the rotary cutter 22b. A cutting pitch is defined by this facing interval.

As described above, in the cutting device 20, the sheet 1 is transferred from the conveying device 10 to the suction unit 23 at the handover position P1, and the sheet 1 is cut when the conveying drum 21 is rotated to the cutting position P2. Then, when the conveying drum 21 is rotated to the fold-back position P3, the flap portion of the sheet 1 is folded back so as to overlap with the diaper body 2, and the disposable diaper 5 is transferred from the cutting device 20 to the transfer device 30 at the transfer position P4.

Hereinafter, with reference to FIG. 6 and FIG. 7, the conveying device 10 which conveys the sheet 1 so as to hand over the sheet 1 to the cutting device 20 on a downstream side is described. Specifically, the conveying device 10 includes: a plurality of suction members 11, 12 having suction surfaces (reference signs being omitted) which are capable of sucking the sheet 1; a conveying device body 13 for rotatably supporting the suction members 11, 12 about a first axis J1 extending in a horizontal direction; a drive device 14 for rotatably driving the suction members 11, 12; and a suction mechanism 15 for giving a suction force to the suction members 11, 12.

The suction member 11 has: a suction part 11a having a suction surface; a pair of mounting plates 11b, 11c extending from the suction part 11a toward the first axis J1 and facing each other in a direction parallel to the first axis J1; sliders 11d, 11e disposed on the respective facing surfaces of the pair of mounting plates 11b, 11c; and a rail 11f disposed on a surface of the mounting plate 11b on a side opposite to the slider 11d. The suction parts 11a are box-like members in each of which a pressure reduction chamber is formed. A pressure in the pressure reduction chamber is reduced by connecting the suction part 11a to a suction source 15a described later. A communication hole is formed in the suction surface of the suction part 11a which faces a side opposite to the first axis J1. The communication hole makes the pressure reduction chamber and the outside of the suction part 11a communicate with each other. The suction surface sucks and holds the sheet 1 when air on the suction surface is sucked through the communication hole. The suction surfaces are surfaces which are formed along the circumference of a circle about the first axis J1.

Figure 8:
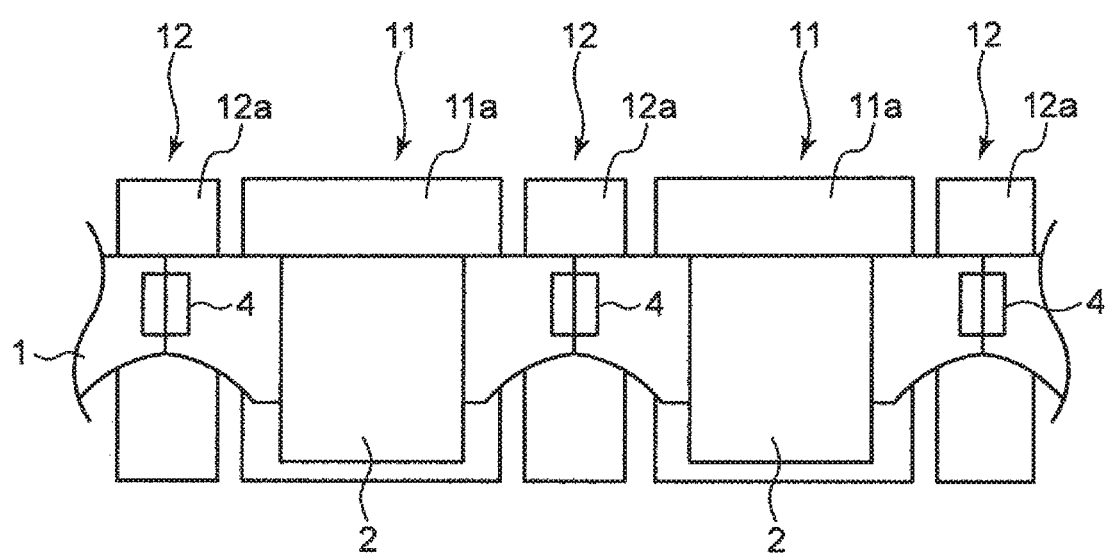
FIG. 8 is a side view showing the relationship between suction parts shown in FIG. 6 and disposable diapers.

The suction member 12 has a configuration similar to that of the suction member 11 except for that the suction member 12 has the suction part 12a having a suction surface in place of the suction part 11a. The suction part 12a has a narrower width size than the suction part 11a in a circumferential direction of the circle about the first axis J1. The suction surface of the suction part 12a also has a width size narrower than a suction surface of the suction part 11a in the circumferential direction. Specifically, as shown in FIG. 8, the suction surface of the suction part 11a has a width size which allows the suction surface to suck the diaper body 2 and portions of the flap portions protruding from both sides of the diaper body 2 in a width direction. On the other hand, the suction surface of the suction part 12a has a width size which allows the suction surface to suck portions of the flap portions projecting from the suction surface of the suction part 11a in a width direction.

Again, with respect to FIG. 6 and FIG. 7, the conveying device body 13 includes: the support member 16 mounted on a mounting surface of the conveying device 10 which is preset; the holding mechanism 17 mounted on the support member 16 such that the holding mechanism 17 is movable relative to the support member 16 in a direction orthogonal to the first axis J1; and a moving device 18 for giving power for moving the holding mechanism 17 relative to the support member 16.

The holding mechanism 17 includes: a support plate 17a to be mounted on the support member 16 described later via a pair of upper and lower sliders 17b, 17c; a cylindrical portion 17d extending from the support plate 17a toward a side opposite to the sliders 17b, 17c in a direction parallel to the first axis J1; a pair of flanges 17e, 17f protruding from an outer peripheral surface of the cylindrical portion 17d in a radial direction of the circle about the first axis J1 and facing each other in a direction parallel to the first axis J1; and rails 17g, 17h respectively mounted on surfaces of the flange 17e, 17f opposite to facing surfaces of the flange 17e, 17f. The flanges 17e, 17f and the rails 17g, 17h are disposed over the entire circumference of the circle about the first axis J1. The pair of flanges 17e, 17f and the rails 17g, 17f are inserted between the mounting plates 11b, 11c of the suction members 11, 12, and the sliders of the suction members 11, 12 slidably engage with the rails 17g, 17f respectively. With such a configuration, the suction members 11, 12 are held on the cylindrical portion 17d in a state where the suction members 11, 12 are movable on a path along the circle about the first axis J1 defined by the rails 17g, 17f.

That is, the holding mechanism 17 holds the suction members 11, 12 in a state where the suction surfaces extend in a spaced-apart manner along the circumference of the circle about the first axis J1 and the plurality of suction members 11, 12 are rotatable about the first axis J1. Specifically, the holding mechanism 17 holds eight suction members 11 and eight suction members 12 such that the suction member 11 and the suction member 12 are alternately arranged along the circumference of the circle about the first axis J1.

Hereinafter, the drive device 14 for rotatably driving the suction members 11, 12 about the first axis J1 is described.

The drive device 14 includes: a motor body 14a fixed to the support member 16 by way of the bracket 16e; a rotary shaft 14b extending from the motor body 14a toward a side opposite to the support member 16; a disc-like connecting plate 14c fixed to the rotary shaft 14b; sixteen connecting pins 14d mounted on a peripheral portion of the connecting plate 14c; and a slider 14e engaged with the rails 11f of the suction members 11, 12.

The motor body 14a has a portion which is supported by the support member 16 by way of the bracket 16e through the inside of the cylindrical portion 17d and is housed in the cylindrical portion 17d; and rotatably drives the rotary shaft 14b about a second axis J2 disposed parallel to the first axis J1. In such a configuration, the cylindrical portion 17d corresponds to a cylindrical holding member body having an outer peripheral surface which extends in a direction parallel to the first axis J1 on one side of the support member 16 and the moving device 18 (support mechanism) in the direction parallel to the first axis J1 and holds the plurality of suction members 11, 12.

The connecting plate 14c, the connecting pin 14d, and the slider 14e correspond to a connecting mechanism configured to connect the rotary shaft 14b extending from the motor body 14a to the position on a side opposite to the support member 16 of the cylindrical portion 17d and the plurality of suction members 11, 12 to each other so as to enable the transmission of power from the rotary shaft 14b to the suction members 11, 12. Specifically, in a state where the connecting plate 14c is fixed to the rotary shaft 14b, a peripheral portion of the connecting plate 14c faces the mounting plate 11b in a direction parallel to the first axis J1 at the position of the mounting plate 11b of the suction members 11, 12 on a side opposite to the mounting plate 11c. The connecting pins 14d extend parallel to the first axis J1, and penetrate the connecting plate 14c in a state where the connecting pin 14d is rotatable relative to the connecting plate 14c about an axis of the connecting pin 14d. End portions of the connecting pins 14d on a side close to the mounting plate 11b are fixed to the slider 14e. The slider 14e engages with the rails 11f in a state where the slider 14e is movable along a longitudinal direction of the rails 11f of the suction members 11, 12. The rails 11f extend along a radial direction of the circle about the first axis J1 in a state where the suction members 11, 12 are held by the holding mechanism 17. In this manner, the connecting mechanism (the connecting plate 14c, the connecting pins 14d, and the slider 14e) is connected to the suction members 11, 12 in a state where the plurality of suction members 11, 12 are movable in the radial direction of the circle about the first axis J1.

The suction mechanism 15 includes: a suction source 15a; a suction duct 15b connected to the suction source 15a and also connected to the mounting plate 11b of the suction members 11, 12 by way of a bracket 15d; and sixteen hoses 15c for connecting the suction duct 15b and the suction parts 11a, 12a of the suction members 11, 12 to each other. By operating the suction source 15a, air in the suction duct 15b, the hoses 15c and the pressure reduction chambers in the suction parts 11a, 12a is sucked. Accordingly, the sheet 1 can be sucked and held by the suction surfaces of the suction members 11, 12.

Hereinafter, the support member 16 on which the holding mechanism 17 is mounted in a state where the holding mechanism 17 is movable in a direction orthogonal to the first axis J1, and the moving device 18 for moving the holding mechanism 17 with respect to the support member 16 are described.

The support member 16 includes: a base plate 16a which is mounted so as to stand on a mounting surface of the preset conveying device 10 and to which the drive device 14 (motor body 14a) is fixed by way of the bracket 16e; a sub plate 16b fixed to a surface of the base plate 16a on a holding mechanism 17 side; and a pair of rails 16c, 16d fixed to a surface of the sub plate 16b on a holding mechanism 17 side. A bracket 16e extends from the motor body 14a to the base plate 16a through holes formed in a support plate 17a and the sub plate 16b. Rails 16c, 16d respectively extend along a direction orthogonal to the first axis J1. Sliders 17b, 17c of the holding mechanism 17 respectively engage with the rails 16c, 16d in a slidable state along a longitudinal direction of the rails 16c, 16d (a directing orthogonal to the first axis J1). In a cylindrical portion 17d of the holding mechanism 17, a support wall 17i for supporting the motor body 14a and the rail 17j fixed to the support wall 17i are disposed. The rail 17j extends in a direction parallel to the rails 16c, 16d of the support members 16. A slider 14f which is fixed to the motor body 14a engages with the rail 17j in a state where the slider 14f is slidable along a longitudinal direction of the rail 17j. In this manner, the support member 16 supports the holding mechanism 17 and the drive device 14 such that the holding mechanism 17 and the drive device 14 are movable relative to each other in a longitudinal direction of the rails 16c, 16d (rail 17j), that is, in a direction orthogonal to the first axis J1.

Figure 7:
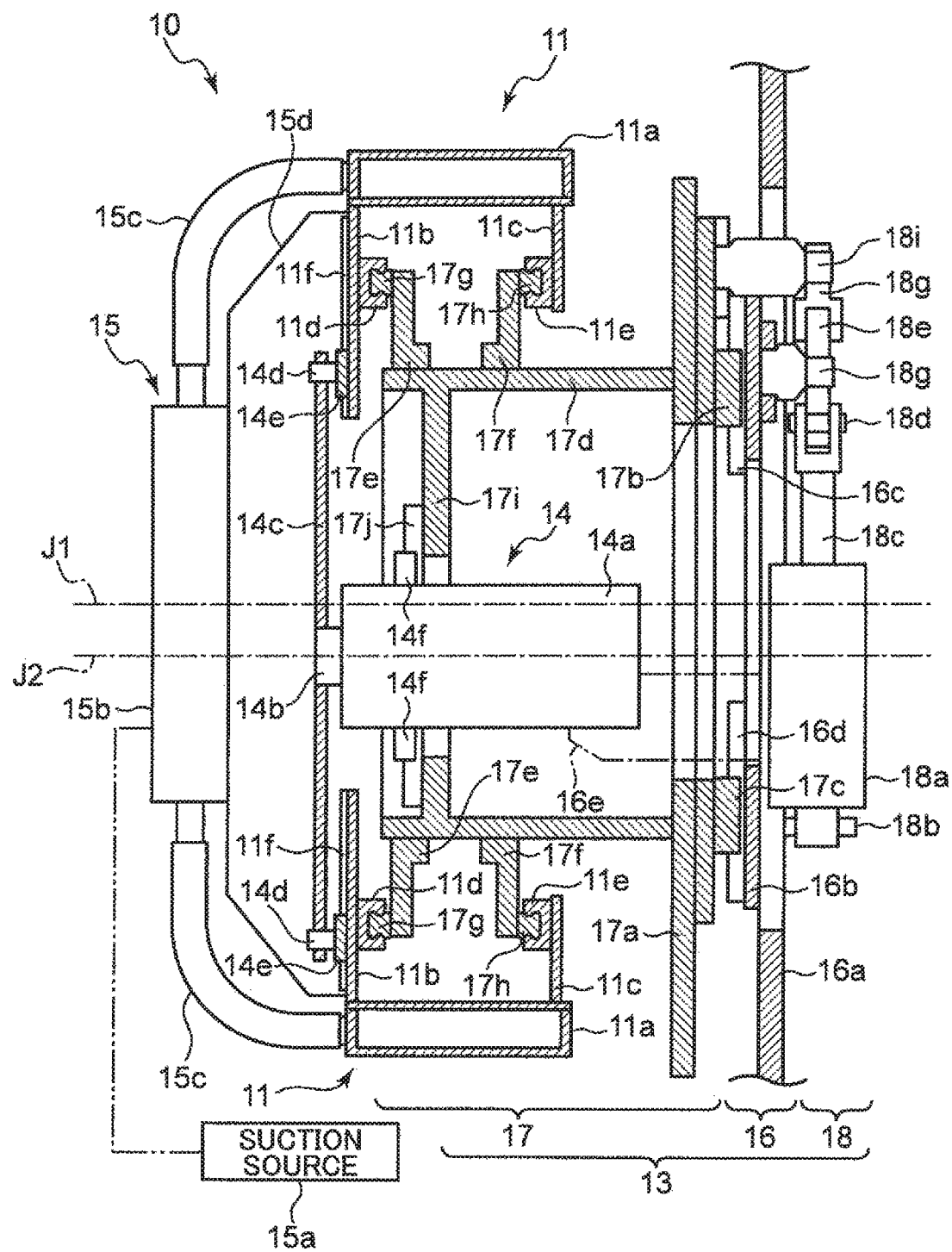
FIG. 7 is a cross-sectional view showing the conveying device shown in FIG. 3 in an enlarged manner.
Figure 9:
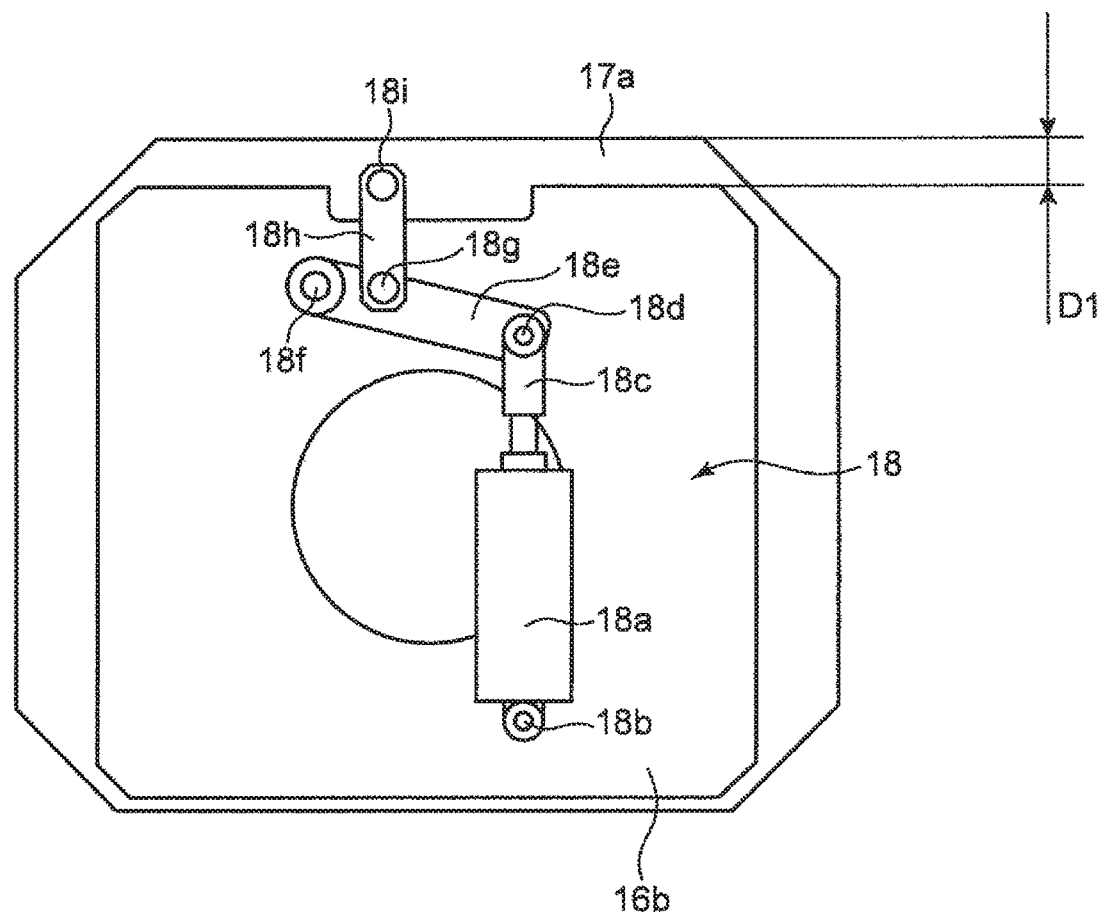
FIG. 9 is a view showing a state before a second supporting member is moved with respect to a first supporting member by a moving device.
Figure 10:
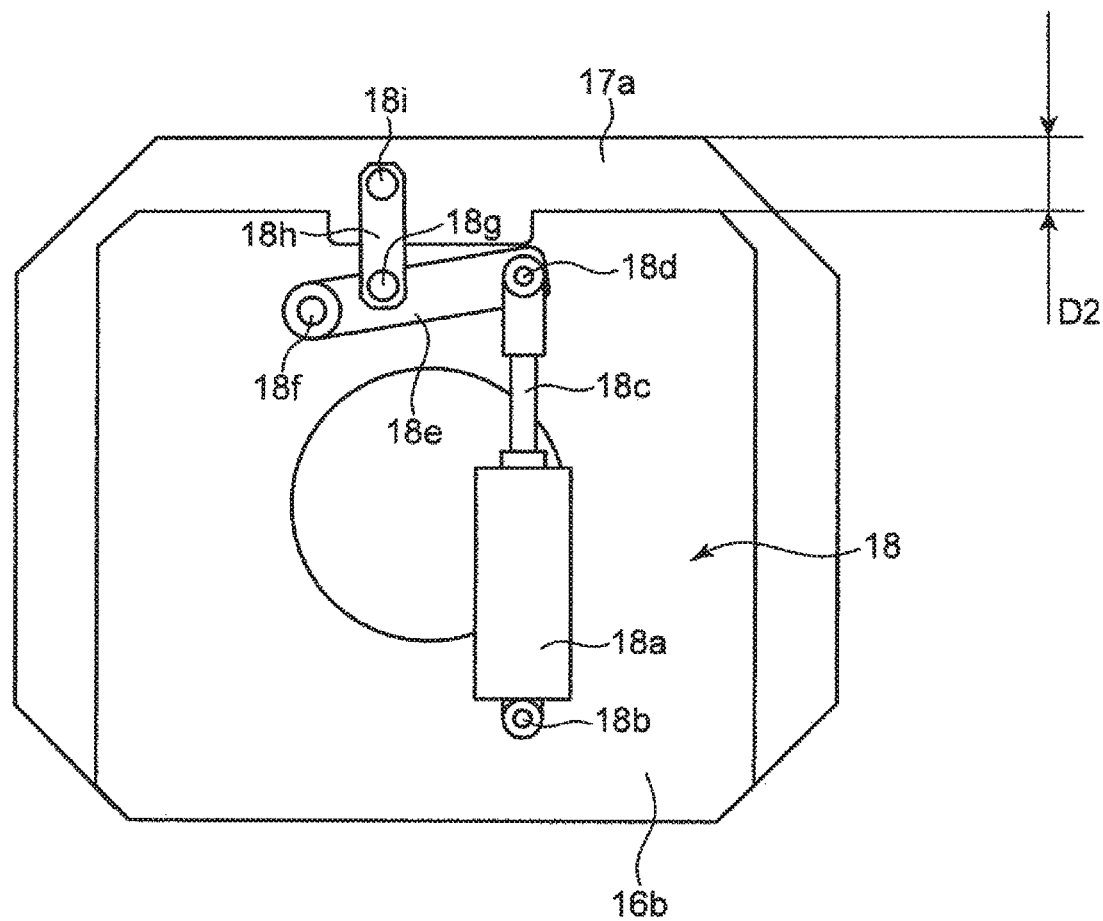
FIG. 10 is a view showing a state after the second supporting member is moved with respect to the first supporting member by the moving device.

FIG. 9 and FIG. 10 are views showing a state where the support member 16 and the moving device 18 shown in FIG. 7 are viewed from a side opposite to the holding mechanism 17. The illustration of the base plate 16a is omitted.

With reference to FIG. 7, FIG. 9, and FIG. 10, the moving device 18 is connected to the holding mechanism 17 and the support member 16. The moving device 18 is provided for giving a force to the holding mechanism 17, the force for moving the holding mechanism 17 in a direction orthogonal to the first axis J1. Specifically, the moving device 18 includes an air cylinder having a cylinder body 18a and a rod 18c. A proximal end portion of the cylinder body 18a is fixed to the base plate 16a in a state where the proximal end portion is rotatable about an axis 18b parallel to the first axis J1. A distal end portion of the rod 18c is mounted on one end portion of a link 18e in a state where the distal end portion is rotatable about an axis 18d parallel to the first axis J1. The other end portion of the link 18e is fixed to the base plate 16a in a state where the other end portion is rotatable about an axis 18f parallel to the first axis J1. An intermediate portion of the link 18e is fixed to one end portion of a link 18h in a state where the intermediate portion is rotatable about an axis 18g parallel to the first axis J1. The other end portion of the link 18h is fixed to the support plate 17a of the holding mechanism 17 in a state where the other end portion is rotatable about an axis 18i parallel to the first axis J1.

When the rod 18c of the air cylinder retracts, the link 18e rotates in a clockwise direction in FIG. 9 about the axis 18f. Accordingly, the link 18h moves downward in FIG. 9. As a result, the support plate 17a, that is, the holding mechanism 17 moves downward in FIG. 9. In such a state, a distance between an end portion of the support plate 17a and an end portion of the sub plate 16b is D1.

On the other hand, when the rod 18c of the air cylinder extends, the link 18e rotates in a counterclockwise direction shown in FIG. 10 about the axis 18f. Accordingly, the link 18h moves upward in FIG. 10. As a result, the support plate 17a, that is, the holding mechanism 17 moves upwards in FIG. 10. In this state, the distance between the end portion of the support plate 17a and the end portion of the sub plate 16b becomes D2 which is larger than D1.

Figure 6:
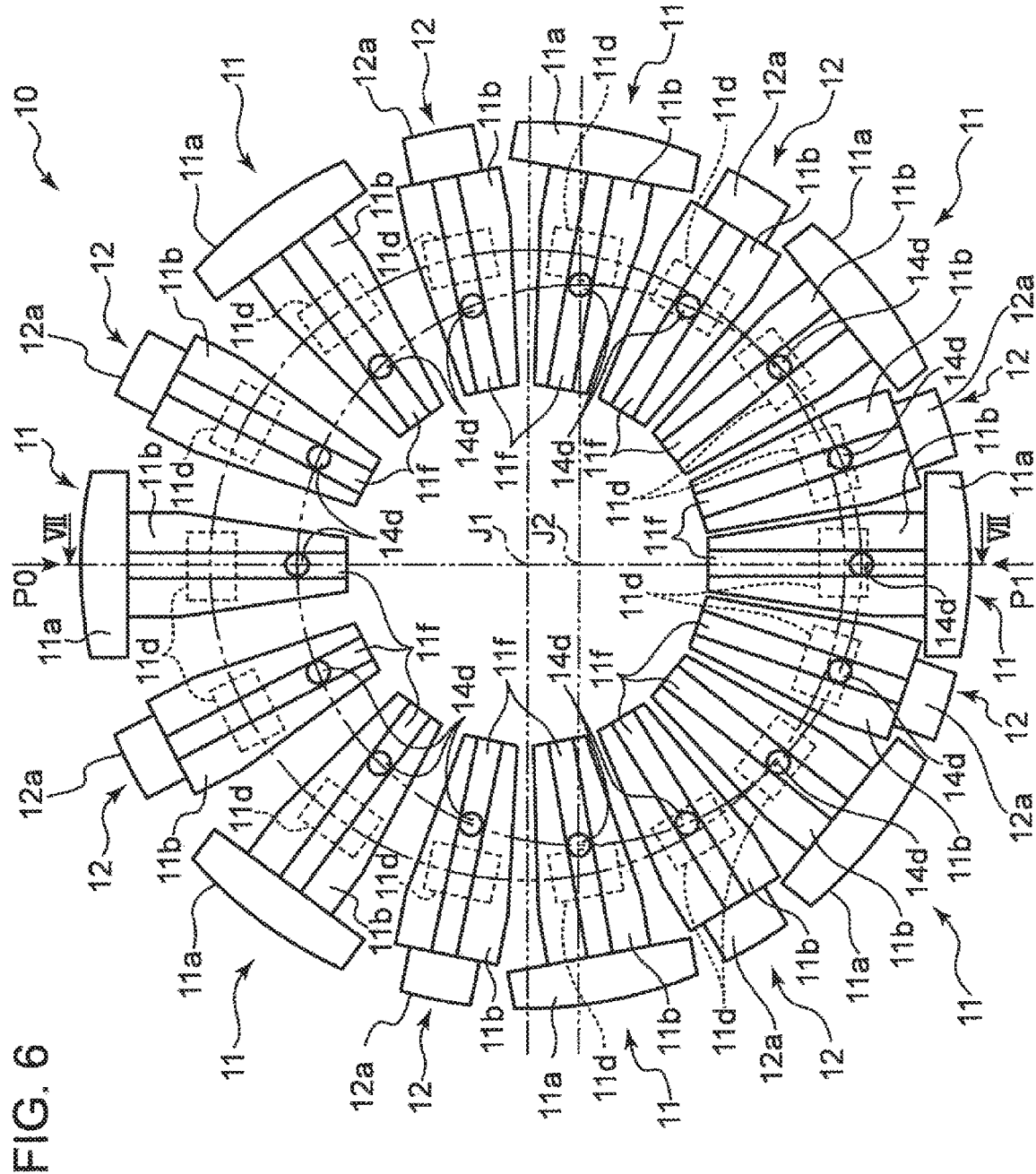
FIG. 6 is a side view showing a conveying device shown in FIG. 3 in an enlarged manner.

In this embodiment, as shown in FIG. 6 and FIG. 9, in a state where the rod 18c of the air cylinder retracts, the support member 16 supports the holding mechanism 17 and the drive device 14 such that the first axis J1 and the second axis J2 are arranged at different positions. In this manner, the first axis J1 and the second axis J2 are arranged at the different positions. Accordingly, the positions of the connecting pins 14d with respect to the suction members 11, 12, that is, a radius (angular velocity) from the second axis J2 which is the center of the rotation to the suction surfaces differ and hence, an interval between the suction surfaces disposed adjacently to each other can be changed in a circumferential direction about the first axis J1. In this embodiment, the receiving position P0 is set at one of two intersecting points between a straight line which passes the first axis J1 and the second axis J2 and the circle about the first axis J1, and the handover position P1 is set at the other of two intersecting points. That is, the position where the interval of the suction surfaces disposed adjacently to each other becomes widest is set as the receiving position P0, and the position where the interval between the suction surfaces disposed adjacently to each other becomes narrowest is set as the handover position P1. Accordingly, a length of the sheet 1 sucked and held by two suction surfaces disposed adjacently to each other can be effetely reduced in a distance from the receiving position P0 to the handover position P1. Step (5), in FIG. 1 can be performed in this manner.

Figure 11:
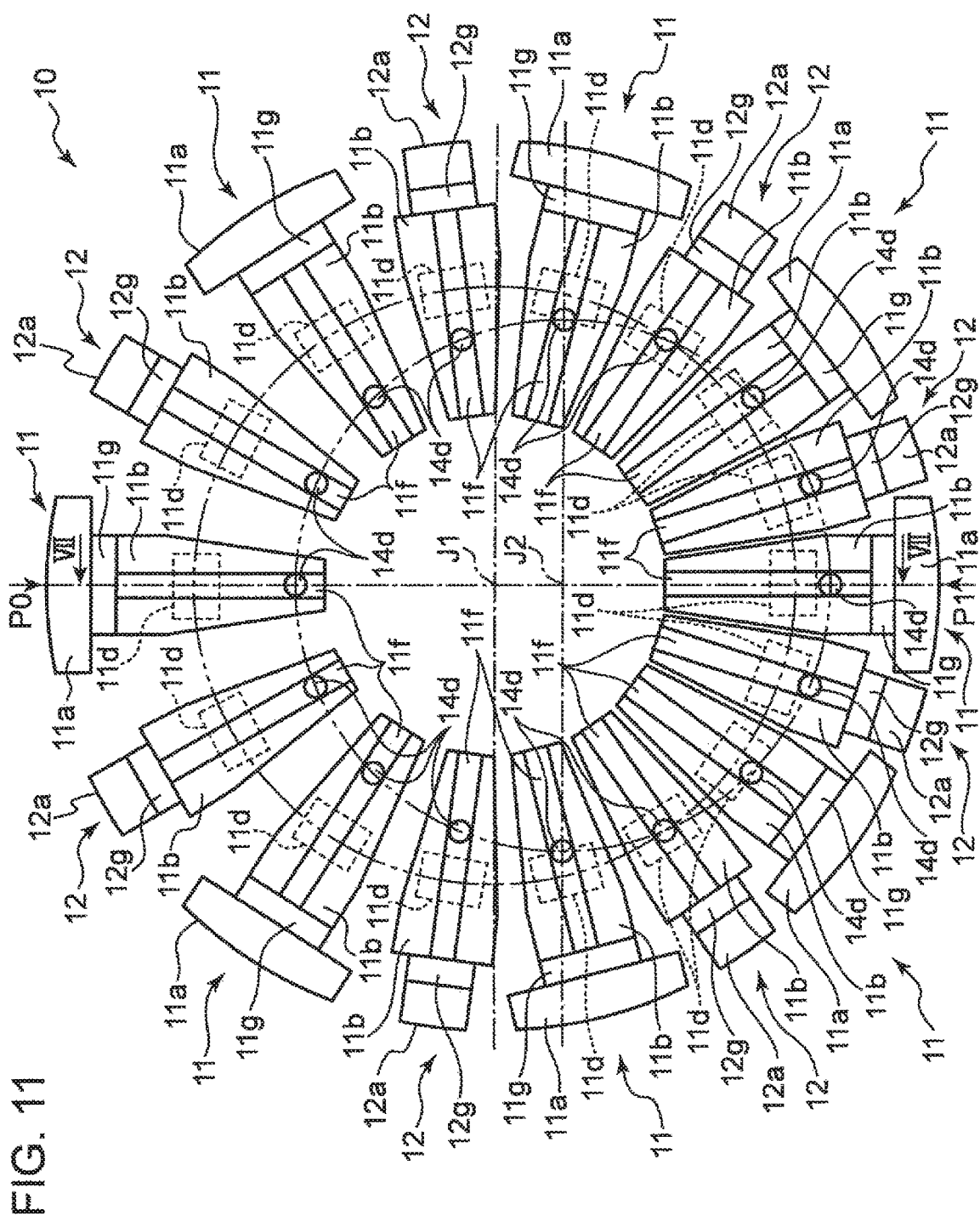
FIG. 11 is a view showing a state where a spacer is disposed between a suction part and a connecting portion.

As shown in FIG. 10 and FIG. 11, when the rod 18c of the air cylinder extends, the first axis J1 moves toward a receiving position P0 side. Accordingly, a distance between the suction surfaces disposed adjacently to each other at the receiving position P0 is increased, while the distance between the suction surfaces disposed adjacently to each other at the handover position P1 is decreased. Accordingly, a length of the sheet 1 sucked and held by two suction surfaces disposed adjacently to each other in the distance from the receiving position P0 to the handover position P1 can be adjusted.

In this case, as described previously, a length of the sheet 1 which the cutting device 20 receives at the handover position P1 is fixed by the distance between the pair of flap sucking parts 23b formed on both sides of the body sucking part 23a of the suction unit 23, that is, by a cutting pitch set by the cutting device 20 (see FIG. 3). Accordingly, at the handover position P1, it is also necessary to set a length of the sheet 1 received from the conveying device 10 at the handover position P1 equal to the above-mentioned length. Accordingly, the suction members 11, 12 further include spacers 11g, 12g which are used only in a second state (a state shown in FIG. 11) when the relative position between the holding mechanism 17 and the drive device 14 is changed from a first state (a state shown in FIG. 6) to the second state such that a distance between two suction surfaces disposed adjacently to each other at the handover position P1 is decreased.

Specifically, the suction members 11, 12 include: the suction parts 11a, 12a; the connecting portions (mounting plates 11b, 11c) which are disposed on a first axis J1 side of the suction parts 11a, 12a in a radial direction of the circle about the first axis J1, and connected to the holding mechanism 17 and the connecting mechanism (the connecting plate 14c, the connecting pins 14d and the slider 14e); and the spacers 11g, 12g which are interposed between the suction parts 11a, 12a and the connecting portions respectively.

The respective spacers 11g, 12g have a thickness size set such that a length of the sheet 1 sucked between two suction surfaces disposed adjacently to each other at the handover position P1 set on the circumference of the circle about the first axis J1 becomes equal between the first state (state shown in FIG. 6) and the second state (shown in FIG. 11). The spacers 11g, 12g are detachably mounted on the suction parts 11a, 12a and the connecting portions. Assuming the relative position between the holding mechanism 17 and the drive device 14 is set to a second state (the state shown in FIG. 11), a rate of a change in a length of the sheet 1 sucked and held by two suction surfaces disposed adjacently to each other in a distance from the receiving position P0 to the handover position P1 is determined based on the relative position of the first axis J1 and the second axis J2, and such a rate is fixed regardless of a radius from the first axis J1 to the suction surfaces. Accordingly, by mounting spacers 11g, 12g having the same thickness size set as described above on all suction members 11, 12, although the circumference of the circle about the first axis J1 which is formed by the suction surface becomes long, a rate of a change in a length of a sheet 1 which changes in the distance from the receiving position P0 to the handover position P1 can be maintained. The length of the sheet 1 at the handover position P1 can be maintained in the first state and the second state and hence, the handover position P1 can be maintained.

Figure 12:
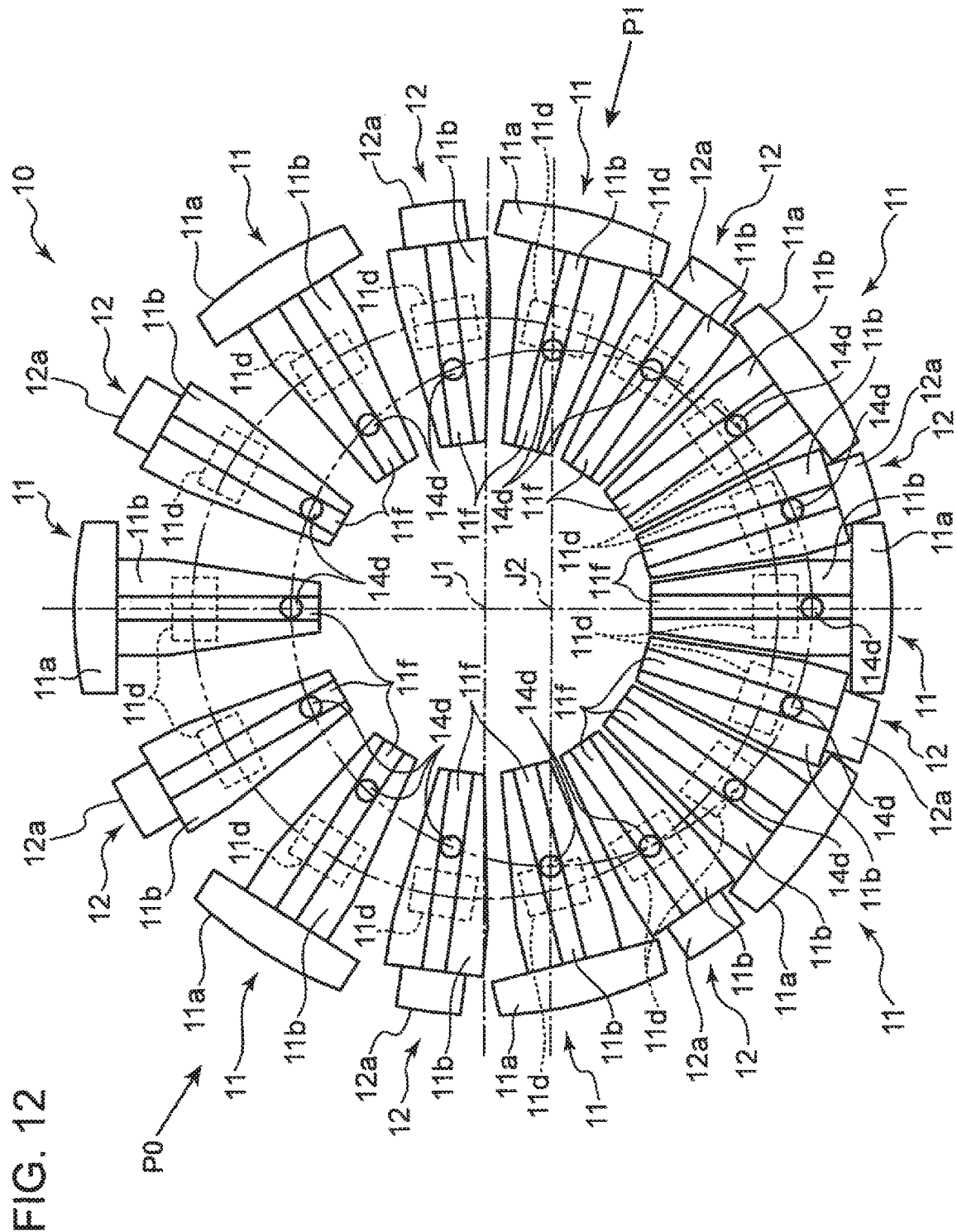
FIG. 12 is a view showing a state where the suction parts and the connecting portions are directly mounted.

As shown in FIG. 12, in the second state, by adjusting at least one of the receiving position P0 and the handover position P1 without using the spacers 11g, 12g, a length of the sheet 1 at the handover position P1 can be adjusted to a length required by the cutting device 20. FIG. 12 shows an example where the receiving position P0 and the handover position P1 are changed.

Hereinafter, a method for conveying the sheet 1 using the conveying device 10 is described.

Firstly, the handover position P1 is set at one of two intersecting points between a straight line which passes the first axis J1 and the second axis J2 and the circle about the first axis J1, and the receiving position P0 is set at the other of two intersecting points (setting step).

Further, the support mechanism is prepared (support mechanism preparing step). The support mechanism includes: the support member 16 to which one of the drive device 14 is fixed; and the moving device 18 which is connected to the holding mechanism 17 and the support member 16, and gives, to the holding mechanism 17, a force for moving the holding mechanism 17 in a direction orthogonal to the first axis J1 with respect to the support member 16.

Then, the rotary shaft 14b is rotatably driven by the motor body 14a about the second axis J2 (first conveying step). Accordingly, the plurality of the suction members 11, 12 are rotated about the first axis J1, and the sheet 1 is conveyed while making the sheet 1 sucked to the suction surfaces of the plurality of the suction members 11, 12.

The sheet 1 conveyed in first conveying step is cut using the cutting device 20 (first cutting step).

In such an operation, for example, when a size of the disposable diaper 5 which is an object to be manufactured is changed, a change of a length of the sheet 1 transferred to the cutting device 20 is requested.

In this case, firstly, rotational driving of the rotary shaft 14b is stopped (stopping step).

Next, the connecting positions between the connecting mechanism (the connecting plate 14c, the connecting pins 14d and the slider 14e) and the suction members 11, 12 are moved in a radial direction of the circle about the first axis J1 by moving the holding mechanism 17 and the drive device 14 relative to each other in a direction orthogonal to the first axis J1 by the support mechanism (the support member 16 and the moving device 18) (moving step). Specifically, in moving step, the relative position between the holding mechanism 17 and the drive device 14 is changed from the first state (see FIG. 6) to the second state (FIG. 11) such that a distance between two suction surfaces disposed adjacently to each other at the handover position P1 is decreased.

In the case where it is necessary to fix the handover position P1 before and after moving step as described above, the plurality of suction members 11, 12 which each have the following configuration are prepared in advance (suction member preparing step). That is, the suction members 11, 12 respectively include: the suction parts 11a, 12a each having the suction surface; the connecting portion (mounting plates 11b, 11c) disposed on a first axis J1 side of the suction parts 11a, 12a in a radial direction of the circle about the first axis J1, and connected to the holding mechanism 17 and the connecting mechanism (the connecting plate 14c, the connecting pins 14d and the slider 14e); and the spacers 11g, 12g disposed detachably between the suction part 11a, 12a and the connecting portion. In such a suction member preparing step, the spacers 11g, 12g are prepared so as to have a thickness size set such that a length of the sheet 1 sucked and held between two suction surfaces disposed adjacently to each other at the handover position P1 becomes equal between the first state and the second state.

Then, the spacers 11g, 12g are mounted between the suction parts 11a, 12a and the connecting portion respectively during a period in which stopping step is performed (mounting step).

After the holding mechanism 17 and the drive device 14 are moved relative to each other in this manner, when necessary, the spacers 11g, 12g are mounted between the suction parts 11a, 12a and the mounting plates 11b, 11c respectively.

Then, the conveyance of the sheet 1 is started again by rotatably driving again the rotary shaft 14b about the second axis J2 (second conveying step).

The sheet 1 conveyed in second conveying step is cut using the cutting device 20 (second cutting step). In first cutting step and second cutting step, the sheet 1 is cut at the same cutting pitch. Further, the relative positional relationship between the sheet conveying device 10 and the cutting device 20 in the circumferential direction of the circle about the first axis J1 is set equal between first cutting step and second cutting step.

As described above, the holding mechanism 17 and the drive device 14 can be moved relative to each other in the direction orthogonal to the first axis J1 by the support mechanism (the support member 16 and the moving device 18) while moving the plurality of the suction members 11, 12 with respect to the connecting member (the connecting plate 14c, the connecting pins 14d, and the slider 14e) in a radial direction of the circle about the first axis J1. Accordingly, the position of the rotary axis (second axis J2) of the drive device 14 can be changed with respective to the first axis J1 in a state where the positions of the suction surfaces are confined on the circumference of the circle about the first axis J1. Therefore, distances from the second axis J2 which corresponds to the center of rotation to the respective suction surfaces, that is, angular velocities of the respective suction surfaces during the rotation are changed and hence, an interval between the suction surfaces disposed adjacently to each other changes on the circumference of the circle about the first axis J1. As a result, a length of the sheet sucked and held by two suction surfaces disposed adjacently to each other can be changed on the circumference of the circle about the first axis J1.

Accordingly, in the case where the sheet 1 is received at the predetermined receiving position P0 on the circumference of a circle about the first axis J1 and the sheet 1 is transferred at the handover position P1, by adjusting the positional relationship between the first axis J1 and the second axis J2, it is possible to easily change the length of the sheet 1 sucked and held by the two suction surfaces disposed adjacently to each other from the receiving position P0 to the handover position P1.

Then, in the cutting device 20 which receives the sheet 1 from the conveying device 10, the sheet is cut at the same cutting pitch in first cutting step and second cutting step. Accordingly, a length of product after completion can be changed by an amount of a length of the sheet 1 at the handover position P1 changed by the conveying device 10.

A distance between the suction surfaces disposed adjacently to each other on the circumference of the circle about the first axis J1 can be continuously changed by adjusting the relative position between the first axis J1 and the second axis J2. Accordingly, even when a cutting pitch is fixed in the cutting device 20 disposed on a downstream side, the sheet 1 can be handed over to the cutting device 20 after a length of the sheet 1 positioned within a cutting pitch is adjusted by changing the receiving position P0 and the handover position P1 on the circumference in the conveying device 10. However, in this case, changing of the length of the sheet 1 positioned within the cutting pitch requires time and efforts for changing the receiving position P0 and the handover position P1 in the conveying device 10.

A rate of a change in a length of the sheet 1 from the receiving position P0 to the handover position P1 of the sheet 1 in the conveying device 10 is determined based on the relative position of the first axis J1 and the second axis J2 and hence, the rate is fixed regardless of a radius from the first axis J1 to the suction surface. Accordingly, when the respective spacers 11g, 12g have the same thickness size set as described above as in the case of the embodiment, a length of the sheet 1 at the handover position P1 can be maintained while maintaining a rate of a change in a length of the sheet 1. In other words, the handover position P1 can be fixed even after a length of the sheet 1 is changed.

In the embodiment, the receiving position P0 or the handover position P1 is set at the position remotest from the first axis J1 (one of two intersecting points) and at the position closest to the first axis J1. Accordingly, a rate of a change in a length of the sheet 1 from the receiving position P0 to the handover position P1 can be set to a maximum value.

According to the embodiment, the holding mechanism 17 and the drive device 14 can be moved relative to each other by the moving device 18 and hence, operability can be enhanced compared to the case where the holding mechanism 17 and the drive device 14 are moved manually.

According to the embodiment, a portion of the motor body 14a is disposed in the cylindrical portion 17d and hence, the motor body 14a and the cylindrical portion (holding member body) 17d can be arranged in an overlapping manner in a direction parallel to the first axis J1.

Accordingly, the downsizing of the conveying device 10 in the same direction can be realized.

In the embodiment, a length of the sheet 1 which the cutting device 20 receives from the conveying device 10 can be set to a fixed value, and a cutting pitch of the cutting device 20 is fixed. Accordingly, a length of the sheet 1 after cutting can be changed by an amount of a length of the sheet 1 on which the length adjustment is made by the conveying device 10. To make a length of the sheet 1 at the handover position in the conveying device 10 consistent with a length of the sheet 1 set at the cutting device 20, it is necessary to use the spacers 11g as described above or to adjust the handover position P1 as shown in FIG. 12. Accordingly, an operation for changing a cutting length of the sheet 1 becomes cumbersome.

In view of the above, with reference to FIG. 13 to FIG. 17, another embodiment is described where an operation for changing a cutting length of the sheet 1 can be more simplified.

FIG. 13 to FIG. 17 are views showing a processing device according to another embodiment which performs the above-mentioned steps (6) to (7) shown in FIG. 1.

The processing device includes: a conveying device 10 which receives a sheet 1 after step (5) is performed at a receiving position P0 and performs step (6); a cutting device 40 which receives the sheet 1 from the conveying device 10 at a handover position P1 and performs step (7); and a transfer device 30 which receives a disposable diaper 5 from the cutting device 40 at a transfer position P4 and transfers the disposable diaper 5 to a step performed on a downstream side. The conveying device 10 and the transfer device 30 have configurations similar to those of the corresponding devices in the embodiment. Accordingly, the description of the devices is omitted below.

Figure 13:
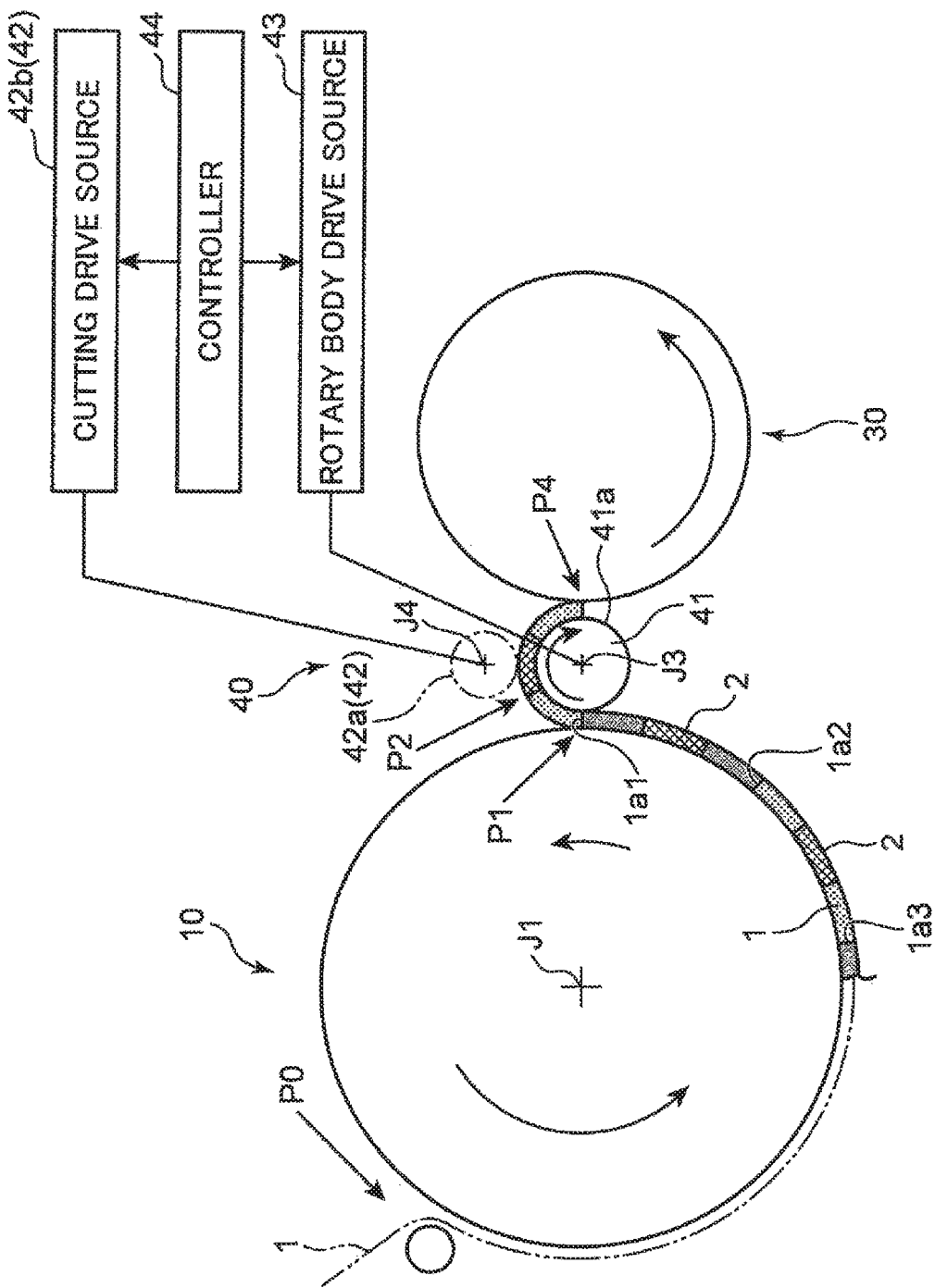
FIG. 13 is a side view showing a portion of a processing device according to another embodiment.
Figure 14:
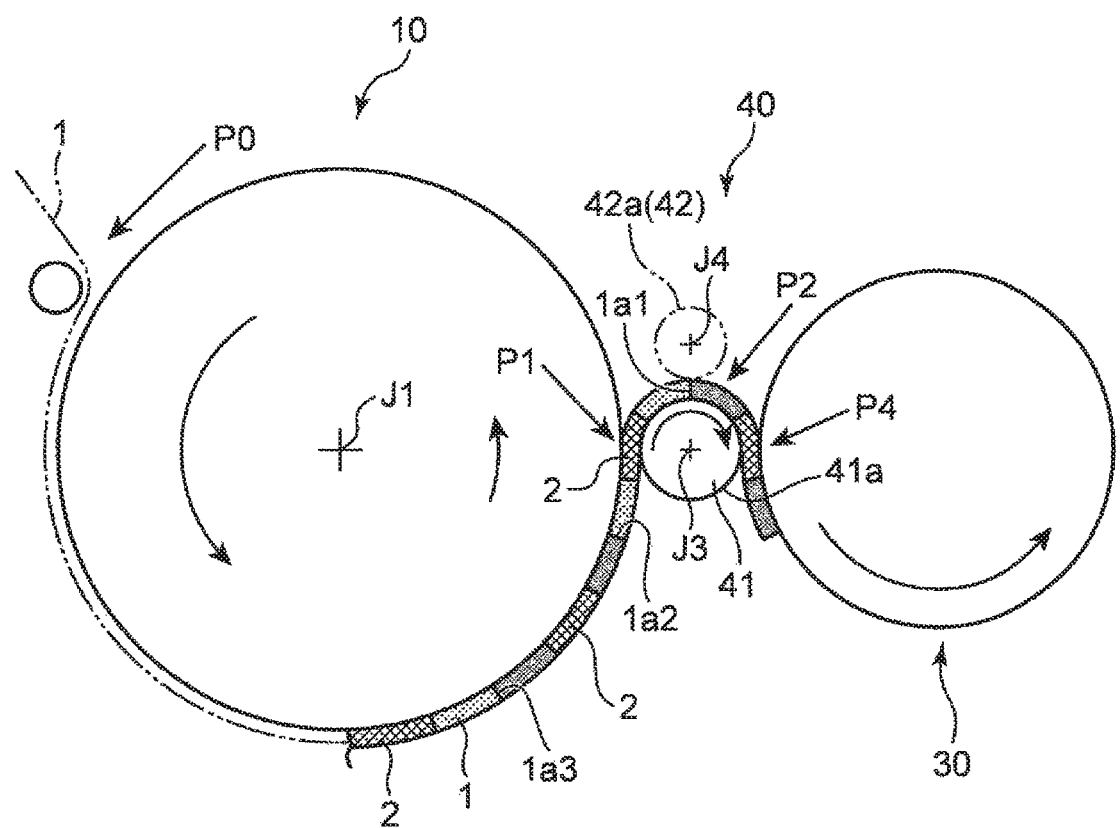
FIG. 14 is a side view showing a cutting state of a sheet in the processing device shown in FIG. 13.
Figure 15:
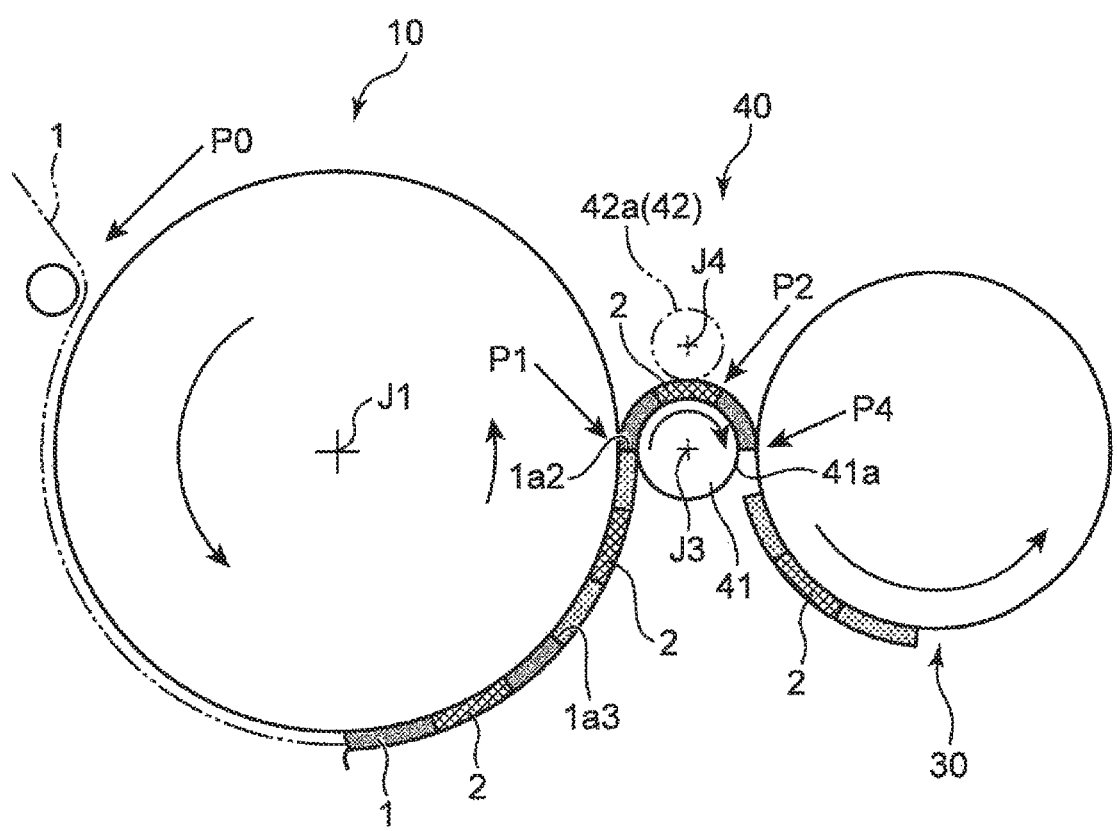
FIG. 15 is a side view showing a state where the sheet cut in the processing device shown in FIG. 13 is transferred to a transfer device.

With reference to FIG. 13, the cutting device 40 includes: a cutting rotary body 41 having an outer peripheral surface 41a which sucks a sheet 1 at a handover position P1; a cutting mechanism 42 for cutting the sheet 1 by clamping the sheet 1 between the outer peripheral surface 41a of the cutting rotary body 41 and the cutting mechanism 42 at a preset time interval; a rotary body drive source 43 for rotatably driving the cutting rotary body 41; and a controller 44 for controlling the rotary body drive source 43.

The cutting rotary body 41 is rotatable about a third axis J3 extending parallel to the first axis J1 of the conveying device 10.

The cutting mechanism 42 includes: a cutting drum 42a disposed in an facing manner with the outer peripheral surface 41a of the cutting rotary body 41 at a cutting position P2; and a cutting drive source 42b for rotatably driving the cutting drum 42a. The cutting drum 42a includes: a drum body; and a cutting blade intermittently mounted on an outer peripheral surface of the drum body in a circumferential direction. The cutting mechanism 42 is configured to cut sheet 1 when the sheet 1 is clamped between the cutting blade and the outer peripheral surface of the cutting rotary body 41 at a predetermined time interval. The cutting drive source 42b is formed of a motor having a rotary shaft connected to the cutting drum 42a such that the rotary shaft is rotatable about a fourth axis J4 extending parallel to the first axis J1.

The rotary body drive source 43 is formed of a servomotor having a rotary shaft connected to the cutting rotary body 41 such that the rotary shaft is rotatable about the third axis J3.

The controller 44 controls the rotary body drive source 43 so as to adjust a speed of the cutting rotary body 41, and controls the cutting drive source 42b so as to adjust a speed of the cutting drum 42a.

FIG. 17 shows the content of a control of the rotary body drive source 43 performed by the controller 44.

With reference to FIG. 17, the controller 44 controls the rotary body drive source 43 such that a length of the sheet 1 which passes a handover position P1 within a time interval where the sheet 1 is clamped between a cutting blade of the cutting mechanism 42 and an outer peripheral surface of the cutting rotary body 41 and a length of the sheet 1 which passes a cutting position P2 within the time interval differ from each other.

Figure 16:
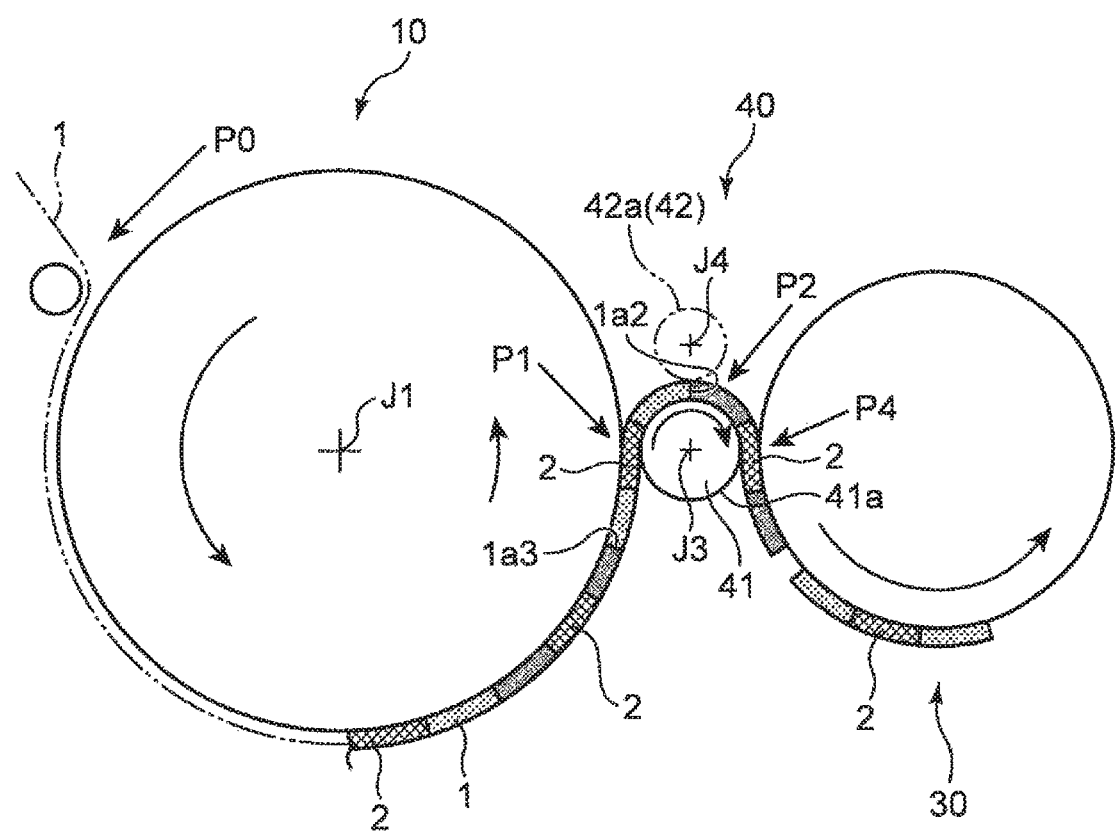

With reference to FIG. 16, a plurality of cutting target positions 1a1 to 1a3 which are preset as positions at which the sheet 1 is cut by the cutting mechanism 42 are set on the sheet 1. As shown in FIG. 17, the controller 44 changes a speed of the cutting rotary body 41 from a point of time that the first cutting target position 1a1 among the cutting target positions 1a1 to 1a3 reaches the handover position P1 (see FIG. 13) to a point of time that the first cutting target position 1a1 reaches the cutting position P2 (see FIG. 14). The controller 44 also changes a speed of the cutting rotary body 41 during a period in which a portion (cut portion) of the sheet 1 corresponding to the first cutting target position 1a1 reaches a transfer position P4 (see FIG. 15) from the cutting position P2. At a point of time that the first cutting target position 1a1 reaches the transfer position P4, the second cutting target position 1a2 succeeding to the first cutting target position 1a1 reaches the handover position P1 (see FIG. 15). Then, the controller 44 changes a speed of the cutting rotary body 41 from a point of time that the second cutting target position 1a2 reaches the handover position P1 to a point of time that the second cutting target position 1a2 reaches the cutting position P2 (see FIG. 16). Then, the controller 44 performs a similar control also with respect to the third cutting target position 1a3 succeeding to the second cutting target position 1a2.

More specifically, as shown in FIG. 17, in the controller 44, a control map C1 for a normal size, a control map C2 for a small size which is smaller than a normal size, and a control map C3 for a large size which is larger than a normal size are stored.

In the control map C1 for a normal size, the controller 44 accelerates a speed of the cutting rotary body 41 during a period that the cutting target positions 1a1 to 1a3 move from the handover position P1 to the cutting position P2, and decelerates the speed of the cutting rotary body 41 during a period that the cutting target positions 1a1 to 1a3 move from the cutting position P2 to the transfer position P4 and returns the speed of the cutting rotary body 41 to the speed before acceleration. With such a control, it is possible to set a length of the sheet 1 which passes the handover position P1 within a time interval of the cutting mechanism 42 longer than a length of the sheet 1 which passes the cutting position P2 within the time interval.

In the control map C2, a speed of the sheet 1 which is transferred from the conveying device 10 at the handover position P1 is set higher than a speed of the sheet 1 set at the time of performing a control in accordance with the control map C1. The controller 44 controls the cutting rotary body 41 such that a speed of the cutting rotary body 41 consists with such a speed of the sheet 1, and decelerates the speed of the cutting rotary body 41 during a period that the cutting target positions 1a1 to 1a3 move from the handover position P1 to the cutting position P2. The decelerated speed of the sheet 1 is lower than a lowest speed in the control map C1. Further, the controller 44 accelerates the speed of the cutting rotary body 41 during a period that the cutting target positions 1a1 to 1a3 move from the cutting position P2 to the transfer position P4 and returns the speed of the cutting rotary body 41 to the speed before deceleration. With such a control, it is possible to make a length of the sheet 1 which passes the handover position P1 within a time interval of the cutting mechanism 42 shorter than a length of the sheet 1 which passes the cutting position P2 within the time interval.

Further, in the control map C3, a speed of the sheet 1 transferred from the conveying device 10 at the handover position P1 is set lower than the speed of the sheet 1 set at the time of performing a control in accordance with the control map C1. The controller 44 controls the cutting rotary body 41 such that a speed of the cutting rotary body 41 consists with such a speed of the sheet 1, and accelerates the speed of the cutting rotary body 41 during a period that the cutting target positions 1a1 to 1a3 move from the handover position P1 to the cutting position P2. The accelerated speed of the sheet 1 is equal to a highest speed in the control map C1. Further, the controller 44 decelerates the speed of the cutting rotary body 41 during a period that the cutting target positions 1a1 to 1a3 move from the cutting position P2 to the transfer position P4 and returns the speed of the cutting rotary body 41 to the speed before acceleration. With such a control, it is possible to make a length of the sheet 1 which passes the handover position P1 within a time interval of the cutting mechanism 42 shorter than a length of the sheet 1 which passes the cutting position P2 within the time interval.

Further, the controller 44 controls a speed of the cutting drum 42a such that a speed of the cutting drum 42a consists with a speed of the sheet 1 at the cutting position P2 controlled as described above.

In processing the sheet 1 using this processing device, the cutting device 40 is prepared (cutting device preparing step).

Then, first conveying step, first cutting step, stopping step, moving step, second conveying step, and second cutting step in the embodiment described previously are performed.

Then, in second cutting step, as described previously, a speed of the cutting rotary body 41 is adjusted such that a length of the sheet 1 which passes the handover position P1 within a time interval is different from a length of the sheet 1 which passes the cutting position P2 within the time interval.

As has been described above, according to the embodiment, it is possible to make a length of the sheet 1 which passes the handover position P1 within a time interval and a length of the sheet 1 which passes the cutting position P2 within the time interval differ from each other. Accordingly, even when a length of the sheet 1 which the cutting rotary body 41 receives from the conveying device 10 at the handover position P1 is any length, it is possible to cut the sheet 1 at a predetermined pitch by controlling a rotational speed of the cutting rotary body 41. Accordingly, a cutting length of the sheet 1 can be easily changed.

In FIG. 17, a rotation zone A1 where a speed of the sheet 1 is fixed corresponds to a zone which the diaper body 2 (an absorbent core in the case where the absorbent core exists) passes the handover position P1 and the transfer position P4. In this manner, by keeping a rotational speed of the cutting rotary body 41 at a fixed speed during the zone where the diaper body 2 passes the handover position P1 and the transfer position P4, the handover of the diaper body 2 from the conveying device 10 to the cutting rotary body 41 and the transfer of the diaper body 2 from the cutting rotary body 41 to the transfer device 30 can be smoothly performed.

The present invention is not limited to the embodiment, and the present invention can adopt the following modes, for example.

In the embodiment, the spacers 11g, 12g are used. However, at least one of the receiving position P0 and the handover position P1 can be changed without using the spacers 11g, 12g.

In the embodiment, the receiving position P0 and the handover position P1 are set on two intersecting points between the straight line which passes the first axis J1 and the second axis J2 and the circle about the first axis J1. However, at least either one of the receiving position P0 or the handover position P1 can be disposed at positions other than these two intersecting points.

In the embodiment, the conveying device 10 used for manufacturing the disposable diaper 5 is exemplified. However, the purpose of using the conveying device 10 is not limited to the disposable diaper 5.

The inventions having the following configurations are mainly included in the above-mentioned specific embodiment.

To overcome the above-mentioned problems, the present invention provides a sheet conveying device for continuously conveying a sheet so as to hand over the sheet to a device disposed on a downstream side, the sheet conveying device including: a plurality of suction members each having a suction surface capable of sucking the sheet; a holding mechanism configured to hold the plurality of suction members in a state where the suction surfaces are arranged in a spaced-apart manner from each other along a circumference of a circle about a first axis and the plurality of suction members is rotatable about the first axis; a drive device having: a rotary shaft being rotatable about a second axis which is parallel to the first axis; and a connecting mechanism configured to connect the rotary shaft and the plurality of suction members to each other such that power from the rotary shaft is transmittable to the plurality of suction members; and a support mechanism configured to support the holding mechanism and the drive device, wherein the connecting mechanism is connected to the plurality of suction members in a state where the plurality of the suction members is movable in a radial direction of the circle about the first axis, and the support mechanism supports the holding mechanism and the drive device such that the holding mechanism and the drive device are relatively movable from each other in a direction orthogonal to the first axis.

According to the present invention, the holding mechanism and the drive device can be moved relative to each other in a direction orthogonal to the first axis by the support mechanism while moving the plurality of suction members with respect to the connecting member in a radial direction of the circle about the first axis. Accordingly, the position of the rotary axis (second axis) of the drive device can be changed with respective to the first axis in a state where the positions of the suction surfaces are confined on the circumference of the circle about the first axis. Therefore, distances from the second axis which corresponds to the center of rotation to the respective suction surfaces, that is, angular velocities of the respective suction surfaces during the rotation are changed and hence, an interval between the suction surfaces disposed adjacently to each other changes on the circumference of the circle about the first axis. As a result, a length of the sheet sucked and held by two suction surfaces disposed adjacently to each other can be changed on the circumference of the circle about the first axis.

Accordingly, in the case where the sheet is received at the predetermined receiving position on the circumference of the circle about the first axis and the sheet is transferred at another handover position, by adjusting the positional relationship between the first axis and the second axis, it is possible to easily change the length of the sheet sucked and held by the two suction surfaces disposed adjacently to each other from the receiving position to the handover position.

A distance between the suction surfaces disposed adjacently to each other on the circumference of the circle about the first axis can be continuously changed by adjusting the relative position between the first axis and the second axis. Accordingly, even when a processing pitch for applying a predetermined processing is fixed in a downstream side device (for example, a conventional cutting pitch), the sheet can be handed over to the device on a downstream side after a length of the sheet to be positioned within a processing pitch is adjusted by changing the receiving position and the handover position on the circumference in the conveying device. However, in this case, changing of the length of the sheet to be positioned within the processing pitch requires time and efforts for changing the receiving position and the handover position in the conveying device.

In view of the above, in the conveying device, it is preferable that the plurality of suction members each include: suction parts each having suction surface; connecting portions disposed on a first axis side of the suction parts in a radial direction of the circle about the first axis and connected to the holding mechanism and the connecting mechanism; and the spacers disposed detachably between the suction parts and the connecting portions, the spacers be used only in a second state when the relative position between the holding mechanism and the drive device is changed from a first state to the second state such that a distance between two suction surfaces disposed adjacently to each other is decreased at the handover position preset on the circumference of the circle about the first axis for handing over the sheet to the device on the downstream side, and the respective spacers in the plurality of suction members have a thickness size set such that a length of the sheet sucked between two suction surfaces disposed adjacently to each other at the handover position becomes equal between the first state and the second state.

A rate of a change in a length of the sheet from the receiving position to the handover position of the sheet in the sheet conveying device is determined based on the relative position of the first axis and the second axis and hence, the rate is fixed regardless of a radius from the first axis to the suction surface. Accordingly, when the respective spacers have the same thickness size set as described above as, a length of the sheet at the handover position can be maintained while maintaining a rate of a change in a length of the sheet. In other words, the handover position can be fixed even after a length of the sheet is changed.

In the sheet conveying device, it is preferable that the handover position be set to one of two intersecting points between the straight line which passes the first axis and the second axis and the circle about the first axis, and the receiving position preset on the circumference of the circle about the first axis for receiving the sheet be set to the other of the two intersecting points.

According to this mode, the receiving position or the handover position is set at the position remotest from the first axis (one of two intersecting points) and at the position closest to the first axis. Accordingly, a rate of a change in a length of the sheet from the receiving position to the handover position can be set to a maximum value.

In the conveying device, it is preferable that the support mechanism include: the support member to which one of the holding mechanism and the drive device is fixed; and the moving device which is connected to the other of the holding mechanism and the drive device and the support member and gives, to the other of the holding mechanism and the drive device, a force for moving the other of the holding mechanism and the drive device with respect to the support member in the direction orthogonal to the first axis.

According to this mode, the holding mechanism and the drive device can be moved relative to each other by the moving device and hence, operability can be enhanced compared to the case where the holding mechanism and the drive device are moved manually.

Although it is not intended to limit the layout of the drive device, it is preferable that, in the conveying device, the holding mechanism include a cylindrical holding member body having an outer peripheral surface which extends in a direction parallel to the first axis on one side of the support mechanism in a direction parallel to the first axis, and holds the plurality of suction members, and the drive device include a motor body having a portion which is supported by the support mechanism through the inside of the holding member body and is housed in the inside of the holding member body, and configured to rotatably drive the rotary shaft, and the connecting mechanism connect the rotary shaft extending from the motor body to the position on a side opposite to the support mechanism of the holding member body and the plurality of suction members to each other.

According to such a mode, the motor body and the holding member body can be arranged in an overlapping manner in a direction parallel to the first axis. Accordingly, the downsizing of the conveying device in the same direction can be realized.

The present invention further provides a sheet processing device for cutting a sheet at a predetermined length, the sheet processing device including: the sheet conveying device; and a cutting device configured to receive the sheet from the sheet conveying device and cut the sheet at a predetermined pitch.

According to the present invention, even when it is necessary to change a length of the sheet positioned within the cutting pitches set by the cutting device, it is possible to easily change the length of the sheet between the pitches by changing the relative position between the holding mechanism and the drive device in the conveying device.

In such a configuration, a length of the sheet which the cutting device receives from the conveying device can be set to a fixed value, and a cutting pitch of the cutting device is fixed. Accordingly, a length of the sheet after cutting can be changed by an amount of a length of the sheet on which the length adjustment is made by the conveying device. However, to make a length of the sheet at the handover position in the conveying device consistent with a length of the sheet set at the cutting device, it is necessary to use the spacers as described above or to adjust the handover position. Accordingly, an operation for changing a cutting length of the sheet becomes cumbersome.

Accordingly, in the processing device, it is preferable that the cutting device include: a cutting rotary body which has an outer peripheral surface for sucking the sheet at the handover position preset on the circumference of the circle about the first axis for causing the conveying device to hand over the sheet to the processing device, and is rotatable about a third axis parallel to the first axis; a cutting mechanism which cuts the sheet by clamping the sheet between the outer peripheral surface of the cutting rotary body and the cutting mechanism at a predetermined time interval at a preset cutting positions; the drive source configured to rotatably drive the cutting rotary body; and a controller which controls the drive source such that a length of the sheet which passes the handover position within a time interval and a length of the sheet which passes the cutting position within the time interval are different from each other.

With such a mode, it is possible to make a length of the sheet which passes the handover position within a time interval and a length of the sheet which passes the cutting position within the time interval differ from each other. Accordingly, even when a length of the sheet which the cutting rotary body receives from the conveying device at the handover position is any length, it is possible to cut the sheet at a predetermined pitch by controlling a rotational speed of the cutting rotary body. Accordingly, a cutting length of the sheet can be easily changed.

The present invention provides a method for conveying a sheet using the sheet conveying device, the method including: a first conveying step of conveying the sheet while making the sheet sucked to the suction surfaces of the plurality of suction members by rotatably driving the rotary shaft about the second axis and thus rotating the plurality of suction members about the first axis; a stopping step of stopping rotary driving of the rotary shaft; a moving step of moving connecting positions between the connecting mechanism and the plurality of suction members in a radial direction of a circle about the first axis by moving the holding mechanism and the drive device relative to each other in a direction orthogonal to the first axis by the support mechanism; and a second conveying step of conveying the sheet by rotatably driving the rotary shaft again about the second axis.

According to the present invention, in the case where it is necessary to change a length of sheet handed over to the device on a downstream side, the rotary shaft is temporarily stopped, and the connecting positions between the connecting mechanism and the suction members are moved in a radial direction of the circle about the first axis by relatively moving the holding mechanism and the drive device from each other. With such a mode, a distance between the suction members disposed adjacently to each other on the circumference of the circle about the first axis can be changed. Accordingly, in the case where the sheet is received at the receiving position on the circumference and the sheet is transferred at the handover position, it is possible to change a length of the sheet held by suction to two suction surfaces disposed adjacently to each other between the receiving position and the handover position.

It is preferable that the method for conveying a sheet further include: a suction member preparing step of preparing the plurality of suction members each including: suction parts each having the suction surface; connecting portions disposed on a first axis side of the suction parts in a radial direction of the circle about the first axis and connected to the holding mechanism and the connecting mechanism; and spacers disposed detachably between the suction parts and the connecting portions; and a mounting step of mounting the spacers between the suction parts and the connecting portions during a period where the stopping step is performed, in the moving step, the relative position between the holding mechanism and the drive device is changed from a first state to a second state such that the distance between two suction surfaces disposed adjacently to each other at the handover position preset on the circumference of the circle about the first axis for handing over the sheet to the device on a downstream side is decreased, and in the suction member preparing step, the spacers be prepared so as to have a thickness size set such that a length of the sheet sucked between two suction surfaces disposed adjacently to each other at the handover position becomes equal between the first state and the second state.

In step of mounting the spacers having the same thickness size set in the above-mentioned manner, by mounting the spacers between the suction parts and the connecting portion, it is possible to maintain a length of the sheet at the handover position while maintaining a rate of a change in the length of the sheet from the receiving position to the handover position. In other words, the handover position can be fixed even after a length of the sheet is changed.

It is preferable that the method for conveying a sheet further include: a setting step of setting the handover position to one of two intersecting points between the straight line which passes the first axis and the second axis and the circle about the first axis, and setting the receiving position preset on the circumference of the circle about the first axis for receiving the sheet to the other of the two intersecting points.

According to this mode, the receiving position or the handover position can be set at the position remotest from the first axis (one of two intersecting points) and at the position closest to the first axis. Accordingly, a rate of a change in a length of the sheet from the receiving position to the handover position can be set to a maximum value.

It is preferable that the method for conveying a sheet further include: a support mechanism preparing step of preparing the support mechanism which includes: the support member to which one of the holding mechanism and the drive device is fixed; and the moving device which is connected to the other of the holding mechanism and the drive device and the support member and gives a force for moving the other of the holding mechanism and the drive device with respect to the support member in the direction orthogonal to the first axis to the other of the holding mechanism and the drive device, and in the moving step, the connecting positions between the connecting mechanism and the plurality of suction members be moved in a radial direction of the circle about the first axis using the moving device.

According to this mode, the holding mechanism and the drive device can be moved relative to each other by the moving device and hence, operability can be enhanced compared to the case where the holding mechanism and the drive device are moved manually.

The present invention further provides a method for processing a sheet using the sheet conveying device, and a cutting device for receiving the sheet from the sheet conveying device and cutting the sheet at a predetermined pitch, the method including: a first conveying step of conveying the sheet while making the sheet sucked to the suction surfaces of the plurality of suction members by rotatably driving the rotary shaft about the second axis and thus rotating the plurality of suction members about the first axis; a first cutting step of cutting the sheet conveyed in the first conveying step using the cutting device; a stopping step of stopping rotary driving of the rotary shaft; a moving step of moving connecting positions between the connecting mechanism and the plurality of suction members in a radial direction of a circle about the first axis by moving the holding mechanism and the drive device relative to each other in a direction orthogonal to the first axis by the support mechanism; a second conveying step of conveying the sheet by rotatably driving the rotary shaft again about the second axis; and a second cutting step of cutting the sheet conveyed in the second conveying step using the cutting device.

According to the present invention, in moving step, a length of the sheet sucked and held by two suction surfaces disposed adjacently to each other can be changed on the circumference of the circle about the first axis.

Accordingly, a length of the sheet which the cutting device receives from the sheet conveying device can be easily changed.

In a method for processing a sheet, it is preferable that the sheet be cut at a same pitch in first cutting step and second cutting step.

With such a mode, in the cutting device which receives the sheet from the conveying device, the sheet is cut at the same cutting pitch in first cutting step and the second cutting step. Accordingly, a length of a product after completion can be changed by an amount of a length of the sheet changed by the sheet conveying device.

It is preferable that the method for processing a sheet further include: a suction member preparing step of preparing a plurality of suction members each including: suction parts each having a suction surface; connecting portions disposed on a first axis side of the suction parts in a radial direction of a circle about the first axis and connected to the holding mechanism and the connecting mechanism; and spacers disposed detachably between the suction parts and the connecting portions; and a mounting step of mounting the spacers between the suction parts and the connecting portions during a period where the stopping step is performed, that in the moving step, the relative position between the holding mechanism and the drive device be changed from a first state to a second state such that the distance between two suction surfaces disposed adjacently to each other at the handover position preset on the circumference of the circle about the first axis for handing over the sheet to the device on a downstream side is decreased, and that in the suction member preparing step, the spacers be prepared so as to have a thickness size set such that a length of the sheet sucked between two suction surfaces disposed adjacently to each other at the handover position is set equal between the first state and the second state, and a relative positional relationship between the sheet conveying device and the cutting device in a circumferential direction of the circle about the first axis be equal in the first cutting step and the second cutting step.

By mounting the spacers between the suction parts and the connecting portion in step of mounting the spacers having the same thickness size set in the above-mentioned manner, it is possible to adjust a length of the sheet at the handover position while maintaining a rate of a change in the length of the sheet from the receiving position to the handover position in the sheet conveying device. Accordingly, in first cutting step and second cutting step, the relative positional relationship between the sheet conveying device and the cutting device in the circumferential direction of the circle about the first axis can be set equal between first cutting step and second cutting step.

In this case, a length of the sheet which the cutting device receives from the conveying device can be set to a fixed value, and a cutting pitch of the cutting device is fixed in first cutting step and second cutting step. Accordingly, a length of the sheet after cutting can be changed by an amount of a length of the sheet on which the length adjustment is made by the conveying device. However, to make a length of the sheet at the handover position in the conveying device consistent with a length of the sheet set by the cutting device, it is necessary to use the spacers as described above or to adjust the handover position. Accordingly, an operation for changing a cutting length of the sheet becomes cumbersome.

Accordingly, it is preferable that the method for processing a sheet further include a cutting device preparing step of preparing the cutting device which includes: the cutting rotary body which has an outer peripheral surface for sucking the sheet at the handover position preset on the circumference of the circle about the first axis for causing the conveying device to hand over the sheet to the processing device, and is rotatable about a third axis parallel to the first axis; and the cutting mechanism which cuts the sheet by clamping the sheet between the outer peripheral surface of the cutting rotary body and the cutting mechanism at a predetermined time interval at a preset cutting positions, and that, in the second cutting step, a speed of the cutting rotary body be adjusted such that a length of the sheet which passes the handover position within the time interval and a length of the sheet which passes the cutting position within the time interval differ from each other.

With such a mode, it is possible to make a length of the sheet which passes the handover position within a predetermined time and a length of the sheet which passes the cutting position within a time interval differ from each other. Accordingly, even when a length of the sheet which the cutting rotary body receives from the conveying device at the handover position is any length, it is possible to cut the sheet at a desired pitch by adjusting a rotational speed of the cutting rotary body. Accordingly, a cutting length of the sheet can be easily changed.

The invention claimed is:

1. A sheet conveying device for continuously conveying a sheet so as to hand over the sheet to a device disposed on a downstream side, the sheet conveying device comprising:
a plurality of suction members each having a suction surface capable of sucking the sheet;
a holding mechanism configured to hold the plurality of suction members in a state where the suction surfaces are arranged in a spaced-apart manner from each other along a circumference of a circle about a first axis and the plurality of suction members is rotatable about the first axis;
a drive device having:
a rotary shaft being rotatable about a second axis which is parallel to the first axis; and
a connecting mechanism configured to connect the rotary shaft and the plurality of suction members to each other such that power from the rotary shaft is transmittable to the plurality of suction members; and
a support mechanism configured to support the holding mechanism and the drive device, wherein
the connecting mechanism is connected to the plurality of suction members in a state where each of the suction members is movable in a radial direction of the circle about the first axis, and
the support mechanism supports the holding mechanism and the drive device such that the first axis of the holding mechanism and the second axis of the drive device are relatively movable from each other in a direction orthogonal to the first axis.

2. The sheet conveying device according to claim 1, wherein
the plurality of suction members each include:
suction parts each having a suction surface;
connecting portions disposed on a first axis side of the suction parts in a radial direction of the circle about the first axis and connected to the holding mechanism and the connecting mechanism; and
spacers disposed detachably between the suction parts and the connecting portions, and
the spacers are used only in a second state when a relative position between the holding mechanism and the drive device is changed from a first state to the second state such that a distance between two suction surfaces disposed adjacently to each other is decreased at the handover position preset on the circumference of the circle about the first axis for handing over the sheet to the device on the downstream side, and
the respective spacers in the plurality of suction members have a thickness size set such that a length of the sheet sucked between two suction surfaces disposed adjacently to each other at the handover position becomes equal between the first state and the second state.

3. The sheet conveying device according to claim 2, wherein the handover position is set to one of two intersecting points between a straight line which passes the first axis and the second axis and the circle about the first axis, and the receiving position preset on the circumference of the circle about the first axis for receiving the sheet is set to the other of the two intersecting points.

4. The sheet conveying device according to claim 3, wherein
the support mechanism includes:
a support member to which one of the holding mechanism and the drive device is fixed; and
a moving device which is connected to the other of the holding mechanism and the drive device and the support member and gives, to the other of the holding mechanism and the drive device, a force for moving the other of the holding mechanism and the drive device with respect to the support member in the direction orthogonal to the first axis.

5. The sheet conveying device according to claim 3, wherein
the holding mechanism includes a cylindrical holding member body having an outer peripheral surface which extends in a direction parallel to the first axis on one side of the support mechanism in a direction parallel to the first axis, and holds the plurality of suction members,
the drive device includes a motor body having a portion which is supported by the support mechanism through the inside of the holding member body and is housed in the inside of the holding member body, and configured to rotatably drive the rotary shaft, and
the connecting mechanism connects the rotary shaft extending from the motor body to the position on a side opposite to the support mechanism of the holding member body and the plurality of suction members to each other.

6. The sheet conveying device according to claim 2, wherein
the support mechanism includes:
a support member to which one of the holding mechanism and the drive device is fixed; and
a moving device which is connected to the other of the holding mechanism and the drive device and the support member and gives, to the other of the holding mechanism and the drive device, a force for moving the other of the holding mechanism and the drive device with respect to the support member in the direction orthogonal to the first axis.

7. The sheet conveying device according to claim 2, wherein
the holding mechanism includes a cylindrical holding member body having an outer peripheral surface which extends in a direction parallel to the first axis on one side of the support mechanism in a direction parallel to the first axis, and holds the plurality of suction members,
the drive device includes a motor body having a portion which is supported by the support mechanism through the inside of the holding member body and is housed in the inside of the holding member body, and configured to rotatably drive the rotary shaft, and
the connecting mechanism connects the rotary shaft extending from the motor body to the position on a side opposite to the support mechanism of the holding member body and the plurality of suction members to each other.

8. The sheet conveying device according to claim 1, wherein
the support mechanism includes:
a support member to which one of the holding mechanism and the drive device is fixed; and
a moving device which is connected to the other of the holding mechanism and the drive device and the support member and gives, to the other of the holding mechanism and the drive device, a force for moving the other of the holding mechanism and the drive device with respect to the support member in the direction orthogonal to the first axis.

9. The sheet conveying device according to claim 8, wherein
the holding mechanism includes a cylindrical holding member body having an outer peripheral surface which extends in a direction parallel to the first axis on one side of the support mechanism in a direction parallel to the first axis, and holds the plurality of suction members,
the drive device includes a motor body having a portion which is supported by the support mechanism through the inside of the holding member body and is housed in the inside of the holding member body, and configured to rotatably drive the rotary shaft, and
the connecting mechanism connects the rotary shaft extending from the motor body to the position on a side opposite to the support mechanism of the holding member body and the plurality of suction members to each other.

10. The sheet conveying device according to claim 1, wherein
the holding mechanism includes a cylindrical holding member body having an outer peripheral surface which extends in a direction parallel to the first axis on one side of the support mechanism in a direction parallel to the first axis, and holds the plurality of suction members,
the drive device includes a motor body having a portion which is supported by the support mechanism through the inside of the holding member body and is housed in the inside of the holding member body, and configured to rotatably drive the rotary shaft, and
the connecting mechanism connects the rotary shaft extending from the motor body to the position on a side opposite to the support mechanism of the holding member body and the plurality of suction members to each other.

11. A sheet processing device for cutting a sheet at a predetermined length, the sheet processing device comprising:
the sheet conveying device according to claim 1; and
a cutting device configured to receive the sheet from the sheet conveying device and cut the sheet at a predetermined pitch.

12. The sheet processing device according to claim 11, wherein
the cutting device includes:
a cutting rotary body which has an outer peripheral surface for sucking the sheet at the handover position preset on the circumference of the circle about the first axis for causing the sheet conveying device to hand over the sheet to the cutting device, and is rotatable about a third axis parallel to the first axis;
a cutting mechanism which cuts the sheet by clamping the sheet between an outer peripheral surface of the cutting rotary body and the cutting mechanism at a predetermined time interval at a preset cutting positions;
a drive source configured to rotatably drive the cutting rotary body; and
a controller which controls the drive source such that a length of the sheet which passes the handover position within a time interval and a length of the sheet which passes the cutting position within the time interval are different from each other.

13. A method for conveying a sheet using the sheet conveying device according to claim 1, the method comprising:
a first conveying step of conveying the sheet while making the sheet sucked to the suction surfaces of the plurality of suction members by rotatably driving the rotary shaft about the second axis and thus rotating the plurality of suction members about the first axis;
a stopping step of stopping rotary driving of the rotary shaft;
a moving step of moving connecting positions between the connecting mechanism and the plurality of suction members in a radial direction of a circle about the first axis by moving the holding mechanism and the drive device relative to each other in a direction orthogonal to the first axis by the support mechanism; and
a second conveying step of conveying the sheet by rotatably driving the rotary shaft again about the second axis.

14. The method for conveying a sheet according to claim 13, further comprising:
a suction member preparing step of preparing the plurality of suction members each including: suction parts each having the suction surface; connecting portions disposed on a first axis side of the suction parts in a radial direction of the circle about the first axis and connected to the holding mechanism and the connecting mechanism; and spacers disposed detachably between the suction parts and the connecting portions; and
a mounting step of mounting the spacers between the suction parts and the connecting portions during a period where the stopping step is performed, wherein
in the moving step, the relative position between the holding mechanism and the drive device is changed from a first state to a second state such that a distance between two suction surfaces disposed adjacently to each other at the handover position preset on the circumference of the circle about the first axis for handing over the sheet to the device on a downstream side is decreased, and in the suction member preparing step, the spacers are prepared so as to have a thickness size set such that a length of the sheet sucked between two suction surfaces disposed adjacently to each other at the handover position becomes equal between the first state and the second state.

15. The method for conveying a sheet according to claim 14, further comprising a setting step of setting the handover position to one of two intersecting points between the straight line which passes the first axis and the second axis and the circle about the first axis, and setting the receiving position preset on the circumference of the circle about the first axis for receiving the sheet to the other of the two intersecting points.

16. The method for conveying a sheet according to claim 13, further comprising a support mechanism preparing step of preparing the support mechanism which includes: the support member to which one of the holding mechanism and the drive device is fixed; and the moving device which is connected to the other of the holding mechanism and the drive device and the support member and gives, to the other of the holding mechanism and the drive device, a force for moving the other of the holding mechanism and the drive device with respect to the support member in the direction orthogonal to the first axis,
wherein in the moving step, the connecting positions between the connecting mechanism and the plurality of suction members are moved in a radial direction of the circle about the first axis using the moving device.

17. A method for processing a sheet using the sheet conveying device according to claim 1, and a cutting device for receiving the sheet from the sheet conveying device and cutting the sheet at a predetermined pitch, the method comprising:
a first conveying step of conveying the sheet while making the sheet sucked to the suction surfaces of the plurality of suction members by rotatably driving the rotary shaft about the second axis and thus rotating the plurality of suction members about the first axis;
a first cutting step of cutting the sheet conveyed in the first conveying step using the cutting device;
a stopping step of stopping rotary driving of the rotary shaft;
a moving step of moving connecting positions between the connecting mechanism and the plurality of suction members in a radial direction of a circle about the first axis by moving the holding mechanism and the drive device relative to each other in a direction orthogonal to the first axis by the support mechanism;
a second conveying step of conveying the sheet by rotatably driving the rotary shaft again about the second axis; and
a second cutting step of cutting the sheet conveyed in the second conveying step using the cutting device.

18. A method for processing a sheet according to claim 17, wherein the sheet is cut at a same pitch in the first cutting step and in the second cutting step.

19. The method for processing a sheet according to claim 17, further comprising:
a suction member preparing step of preparing a plurality of suction members each including: suction parts each having a suction surface; connecting portions disposed on a first axis side of the suction parts in a radial direction of the circle about the first axis and connected to the holding mechanism and the connecting mechanism; and spacers disposed detachably between the suction parts and the connecting portions; and
a mounting step of mounting the spacers between the suction parts and the connecting portions during a period where the stopping step is performed, wherein
in the moving step, the relative position between the holding mechanism and the drive device is changed from a first state to a second state such that a distance between two suction surfaces disposed adjacently to each other at the handover position preset on the circumference of the circle about the first axis for handing over the sheet to the device on a downstream side is decreased,
in the suction member preparing step, the spacers are prepared so as to have a thickness size set such that a length of the sheet sucked between two suction surfaces disposed adjacently to each other at the handover position is set equal between the first state and the second state, and
a relative positional relationship between the sheet conveying device and the cutting device in a circumferential direction of the circle about the first axis is equal in the first cutting step and the second cutting step.

20. The method for processing a sheet according to claim 17, further comprising a cutting device preparing step of preparing a cutting device which includes: a cutting rotary body which has an outer peripheral surface for sucking the sheet at the handover position preset on the circumference of the circle about the first axis for causing the sheet conveying device to hand over the sheet to the cutting device, and is rotatable about a third axis parallel to the first axis; and the cutting mechanism which cuts the sheet by clamping the sheet between the outer peripheral surface of the cutting rotary body and the cutting mechanism at a predetermined time interval at a preset cutting positions,
wherein, in the second cutting step, a speed of the cutting rotary body is adjusted such that a length of the sheet which passes the handover position within the time interval and a length of the sheet which passes the cutting position within the time interval differ from each other.

* * * * *